(12) United States Patent
Lowery

(10) Patent No.: US 11,375,953 B2
(45) Date of Patent: Jul. 5, 2022

(54) MEDICAL DEVICES WITH LAYERED CONDUCTIVE ELEMENTS AND METHODS FOR MANUFACTURING THE SAME

(71) Applicant: ECOM Medical, Inc., San Juan Capistrano, CA (US)

(72) Inventor: Guy Russell Lowery, San Juan Capistrano, CA (US)

(73) Assignee: ECOM Medical, Inc., San Juan Capistrano, CA (US)

( * ) Notice: Subject to any disclaimer, the term of this patent is extended or adjusted under 35 U.S.C. 154(b) by 107 days.

(21) Appl. No.: 17/013,581

(22) Filed: Sep. 5, 2020

(65) Prior Publication Data

US 2020/0397376 A1   Dec. 24, 2020

Related U.S. Application Data

(63) Continuation of application No. 16/325,179, filed as application No. PCT/US2017/046662 on Aug. 12, 2017, now Pat. No. 10,799,181.

(Continued)

(51) Int. Cl.
  *A61B 5/00*       (2006.01)
  *A61B 5/026*      (2006.01)
  (Continued)

(52) U.S. Cl.
  CPC ............ *A61B 5/6847* (2013.01); *A61B 5/026* (2013.01); *A61B 5/02416* (2013.01);
  (Continued)

(58) Field of Classification Search
  CPC ... A61B 5/02416; A61B 5/026; A61B 5/0421; A61B 5/0538; A61B 5/14551;
  (Continued)

(56) References Cited

U.S. PATENT DOCUMENTS 5,163,927 A  11/1992  Woker et al.
5,193,533 A   3/1993  Body et al.
(Continued)

FOREIGN PATENT DOCUMENTS

WO  WO2014168987 A1  10/2014
WO  WO2016094938 A9   6/2016
(Continued)

OTHER PUBLICATIONS

PCT International Search Report and Written Opinion for PCT/US2017/046662, ECOM Medical, Inc., Forms PCT/ISA/220, 210, and 237 dated Dec. 21, 2017 (26 pages).

*Primary Examiner* — Erin M Piateski
(74) *Attorney, Agent, or Firm* — Blair Walker IP Services, LLC

(57) ABSTRACT

A system for performing a diagnostic or therapeutic procedure within a subject includes a device having a distal portion configured for insertion within a lumen or duct of the subject, the device including an elongate body having a longitudinal axis, the elongate body comprising a polymeric material and having a proximal end and a distal end, one or more electrically-conductive tracings carried on a first surface of the elongate body and configured to carry a signal, and one or more conductors embedded within the polymeric material and configured to carry a signal.

20 Claims, 22 Drawing Sheets

Related U.S. Application Data

(60) Provisional application No. 62/374,794, filed on Aug. 13, 2016.

(51) Int. Cl.

| | | |
|---|---|---|
| *A61B 5/024* | (2006.01) | |
| *A61B 5/1455* | (2006.01) | |
| *A61B 5/0538* | (2021.01) | |
| *A61B 5/285* | (2021.01) | |
| *A61N 1/05* | (2006.01) | |
| *A61B 18/14* | (2006.01) | |
| *A61M 16/12* | (2006.01) | |
| *A61M 16/04* | (2006.01) | |
| *A61B 5/029* | (2006.01) | |

(52) U.S. Cl.
CPC ........ *A61B 5/0538* (2013.01); *A61B 5/14551* (2013.01); *A61B 5/285* (2021.01); *A61B 5/687* (2013.01); *A61B 5/6852* (2013.01); *A61B 5/029* (2013.01); *A61B 5/6851* (2013.01); *A61B 5/6853* (2013.01); *A61B 18/1492* (2013.01); *A61B 2562/12* (2013.01); *A61M 16/0409* (2014.02); *A61M 16/12* (2013.01); *A61M 2202/0208* (2013.01); *A61N 1/0507* (2013.01); *A61N 1/0517* (2013.01); *A61N 1/0519* (2013.01)

(58) Field of Classification Search
CPC ....... A61B 5/687; A61B 5/029; A61B 5/6851; A61B 5/6853; A61B 18/1492; A61B 2562/12; A61M 16/0409; A61M 16/12; A61M 2202/0208; A61N 1/0507; A61N 1/0517; A61N 1/0519
USPC .......................................................... 600/300
See application file for complete search history.

(56) References Cited

U.S. PATENT DOCUMENTS

| | | |
|---|---|---|
| 5,372,603 A | 12/1994 | Acker et al. |
| 5,379,765 A | 1/1995 | Kajiwara et al. |
| 5,782,774 A | 7/1998 | Shmulewitz |
| 5,791,349 A | 8/1998 | Shmulewitz |
| 6,095,987 A | 8/2000 | Shmulewitz et al. |
| 6,292,689 B1 | 9/2001 | Wallace et al. |
| 7,229,437 B2 | 6/2007 | Johnson et al. |
| 7,234,225 B2 | 6/2007 | Johnson et al. |
| 8,805,466 B2 | 8/2014 | Salahieh et al. |
| 8,808,532 B2 | 8/2014 | Yang et al. |
| 9,028,472 B2 | 5/2015 | Mathur et al. |
| 9,016,134 B2 | 6/2015 | Askin, III et al. |
| 9,579,152 B2 | 2/2017 | Prakash et al. |
| 9,707,034 B2 | 6/2017 | Schaer |
| 2002/0133081 A1 | 9/2002 | Ackerman et al. |
| 2003/0176816 A1 | 9/2003 | Maguire et al. |
| 2004/0249337 A1 | 12/2004 | DiFiore |
| 2005/0065586 A1 | 3/2005 | Johnson |
| 2005/0165301 A1 | 7/2005 | Smith et al. |
| 2005/0210672 A1 | 9/2005 | Reynolds et al. |
| 2007/0005052 A1 | 1/2007 | Kampa et al. |
| 2008/0004618 A1* | 1/2008 | Johnson ............... A61B 5/6852 606/41 |
| 2010/0228202 A1* | 9/2010 | O'Dea ............. A61M 25/1027 156/60 |
| 2011/0072659 A1 | 3/2011 | Swanson et al. |
| 2012/0130363 A1 | 5/2012 | Kim et al. |
| 2012/0204867 A1 | 8/2012 | Levitan |
| 2012/0215074 A1 | 8/2012 | Krimsky |
| 2012/0323089 A1 | 12/2012 | Feer et al. |
| 2013/0085416 A1 | 4/2013 | Mest |
| 2013/0144145 A1 | 6/2013 | Meng |
| 2013/0338480 A1 | 12/2013 | Hann |
| 2014/0228838 A1 | 8/2014 | Kirschenman |
| 2014/0243821 A1 | 8/2014 | Salahieh et al. |
| 2014/0257068 A1 | 9/2014 | Anderson et al. |
| 2014/0257281 A1 | 9/2014 | Squire et al. |
| 2014/0357956 A1* | 12/2014 | Salahieh ............ A61B 1/00181 348/77 |
| 2015/0025532 A1 | 1/2015 | Hanson et al. |
| 2015/0148877 A1 | 5/2015 | Thakkar et al. |
| 2015/0173773 A1 | 6/2015 | Bowman et al. |
| 2015/0366508 A1 | 12/2015 | Chou et al. |
| 2016/0129223 A1 | 5/2016 | Kirschenman |
| 2016/0287278 A1 | 10/2016 | Stigall et al. |
| 2016/0296744 A1 | 10/2016 | Chen et al. |
| 2016/0338647 A1 | 11/2016 | Sterrett et al. |
| 2016/0345857 A1* | 12/2016 | Jensrud ................. A61B 5/065 |
| 2017/0231572 A1 | 8/2017 | Lowery |

FOREIGN PATENT DOCUMENTS

| | | |
|---|---|---|
| WO | WO2016179563 A1 | 11/2016 |
| WO | WO2017142980 A1 | 8/2017 |

\* cited by examiner

MEDICAL DEVICES WITH LAYERED CONDUCTIVE ELEMENTS AND METHODS FOR MANUFACTURING THE SAME

INCORPORATION BY REFERENCE TO ANY PRIORITY APPLICATIONS

This application is a continuation of U.S. patent application Ser. No. 16/325,179, filed on Feb. 12, 2019, which is a U.S. National Stage patent application for PCT application no. PCT/US2017/046662, filed on Aug. 12, 2017, which claims the benefit of priority to U.S. Provisional Application No. 62/374,794, filed on Aug. 13, 2016, all of which are incorporated by reference in their entirety herein for all purposes. Priority is claimed pursuant to 35 U.S.C. § 120 and 35 U.S.C. § 119.

BACKGROUND

A variety of medical devices are manufactured and utilized which incorporate conductors, sensors, electrodes, circuits, or other electrical elements on elongate shafts or tubing. These medical devices are used in diagnostic and/or therapeutic procedures, in which it is desired to carry a signal either toward the patient or away from the patient along the elongate shaft of the medical device. In many cases, the diameter or transverse dimension of the shaft must be as small as possible, so that it may better fit through a natural or medically-created orifice in the body of the patient, or fit down a natural or medically-created space in the body of the patient.

SUMMARY OF THE INVENTION

In one embodiment of the present disclosure, a system for performing a diagnostic or therapeutic procedure within a subject includes a device having a distal portion configured for insertion within a lumen or duct of the subject, the device including an elongate body having a longitudinal axis, the elongate body comprising a polymeric material and having a proximal end and a distal end, one or more electrically-conductive tracings carried on a first surface of the elongate body and configured to carry a signal, and one or more conductors embedded within the polymeric material and configured to carry a signal.

In another embodiment of the present disclosure, an elongate body of a device having a distal portion configured for insertion within a subject is made by a process including the steps of obtaining an elongate member having an outer surface, obtaining a first tubular member having an outer surface and an inner surface, everting a first length of the first tubular member such that at least a portion of the inner surface is exposed, applying one or more electrically-conductive tracings to the everted inner surface of the first tubular member, reverting at least some of the first length of the first tubular member, such that at least a portion of the one or more electrically-conductive tracings is internally-facing, and coupling the first tubular member over the elongate member.

In yet another embodiment of the present disclosure, a method of forming an elongate body of a device having a distal portion configured for insertion within a subject includes obtaining an elongate member having an outer surface, obtaining a first tubular member having an outer surface and an inner surface, everting a first length of the first tubular member such that at least a portion of the inner surface is exposed, applying one or more electrically-conductive tracings to the everted inner surface of the first tubular member, reverting at least some of the first length of the first tubular member, such that at least a portion of the one or more electrically-conductive tracings is internally-facing, and coupling the first tubular member over the elongate member.

In still another embodiment of the present disclosure, an elongate body of a device having a distal portion configured for insertion within a subject is made by a process including the steps of obtaining an elongate member having an outer surface, applying one or more electrically-conductive tracings to the outer surface of the elongate member, adding an annular layer over the elongate member and the one or more electrically-conductive tracings of the elongate member, the annular layer having an outer surface, and applying one or more electrically-conductive tracings to the outer surface of the annular layer.

In yet another embodiment of the present disclosure, a method of forming an elongate body of a device having a distal portion configured for insertion within a subject includes obtaining an elongate member having an outer surface, applying one or more electrically-conductive tracings to the outer surface of the elongate member, adding an annular layer over the elongate member and the one or more electrically-conductive tracings of the elongate member, the annular layer having an outer surface, and applying one or more electrically-conductive tracings to the outer surface of the annular layer.

In still another embodiment of the present disclosure, a system for performing a diagnostic or therapeutic procedure within a subject includes a device having a distal portion configured for insertion within the subject, the device including an elongate shaft having a proximal end and a distal end, first and second electrically-conductive tracings carried by the elongate shaft, wherein the first electrically-conductive tracing is carried on a first surface of the elongate shaft and the second electrically-conductive tracing is carried on a second surface of the elongate shaft, and an inflatable cuff carried on the distal portion of the device.

In yet another embodiment of the present disclosure, a system for diagnosis or therapy includes a device having a distal portion configured for insertion within a subject, the device including an elongate body having a proximal end and a distal end, and first and second electrically-conductive tracings carried by the elongate body, wherein the first electrically-conductive tracing is carried on a first surface of the elongate body and the second electrically-conductive tracing is carried on a second surface of the elongate body.

In still another embodiment of the present disclosure, a system for performing a diagnostic or therapeutic procedure within a subject includes a device having a distal portion configured for insertion within a lumen or duct of the subject, the device including an elongate body having a proximal end and a distal end, and first and second electrically-conductive tracings carried by the elongate body, the first electrically-conductive tracing electrically isolated from the second electrically-conductive tracing, wherein the first electrically-conductive tracing is carried on a first inner-facing surface of the elongate body and the second electrically-conductive tracing is carried on a first outer-facing surface of the elongate body.

In yet another embodiment of the present disclosure, a system for performing a diagnostic or therapeutic procedure within a subject includes a device having a distal portion configured for insertion within a lumen or duct of the subject, the device including an elongate body having a longitudinal axis, the elongate body comprising a polymeric material and having a proximal end and a distal end, one or more electrically-conductive tracings carried on a first surface of the elongate body and configured to carry a signal, and one or more conductors carried within the polymeric material and configured to carry a signal.

DETAILED DESCRIPTION OF THE ILLUSTRATED EMBODIMENTS

One shortcoming that limits the ability to manufacture a medical device incorporating multiple sensors, electrodes and/or circuits (e.g., for monitoring or treating a patient) is that there are limits to the number of circuit wires and/or conductive tracings (also called traces) that can be utilized for a particular size of a device. This is evident on devices that are intended to be introduced into the body where a natural lumen such as a vein, artery, trachea or esophagus will be utilized. As an example, a nasal gastric tube is introduced into the stomach through the nose and down the descending esophagus. The tube often being approximately 4 mm in diameter, it is difficult to print/deposit or place linear wires/conductive tracings on the surface to connect with sensors. Because there are often additional current and isolation requirements for the device, one may only be able to deposit three or four conductive tracings on the surface of the device, when more may be needed or desired. The present disclosure overcomes these limitations while having minimal or no impact on device diameter. Utilizing a thin tubular membrane one can deposit tracings on the outside surface of the tubular membrane. One can then turn the membrane inside-out over at least a portion of the length of the tubular membrane and place the tracings in the everted inside surface. and one may then cover the tracings with a thin insulating/dielectric coating. One can then also place similar tracings on the outside surface or other portions of the medical device shaft. By then reverting the membrane over the medical device shaft the cross-section now includes (from the inside, out) the original NG tube, a layer of conductive tracings, a dielectric, another layer of conductive tracings, the insulated tubular membrane, a third layer of conductive tracings, and a final dielectric coating. The resulting device now has three times the number of conductive tracings as the original. This can even be repeated with a second membrane to add two more conductive tracing layers. Each tracing can then be accessed at either end or through the membrane to make connection with the sensor/electrode or resistive component, dependent upon the desired function. At the proximal end of the tracings, each tracing can be accessed to make a connection to a connector, configured to plug in to a console. The word "evert" as used herein shall be defined as "to turn outward." The word "revert" as used herein shall be defined as "to return to a former condition or orientation."

This concept can also be applied in various geometric configurations including flat or other configurations and in flexible, inflatable or rigid formats dependent upon desired function.

Figure 1:
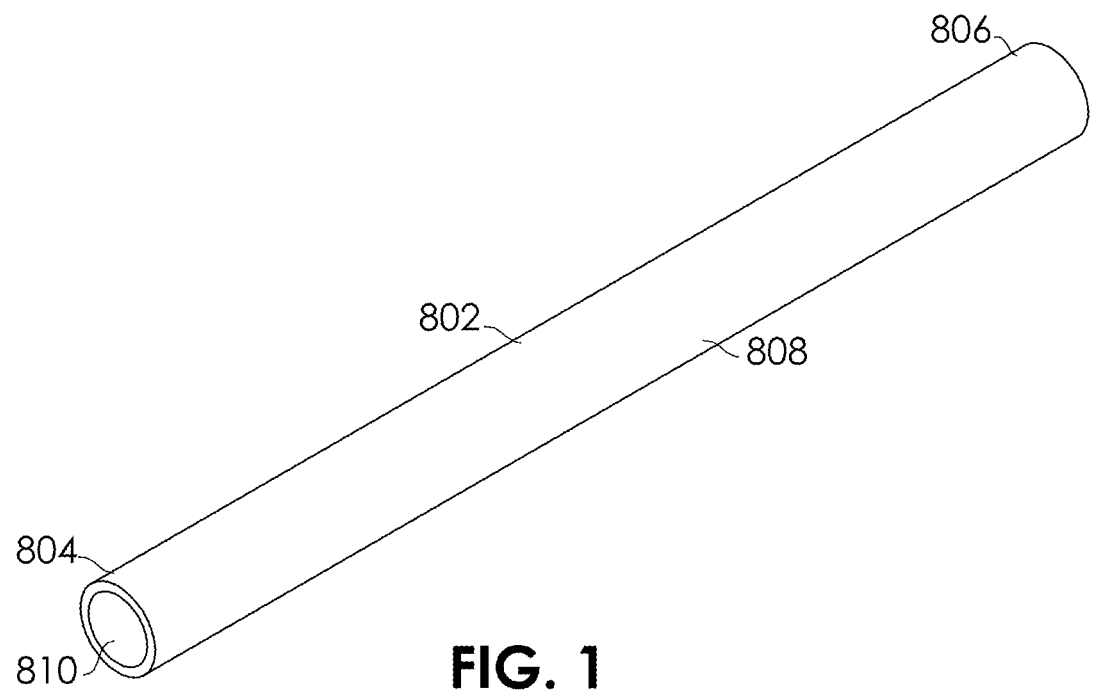
FIG. 1 is a perspective view of a tubular component of a medical device according to an embodiment of the present disclosure.
Figure 2:
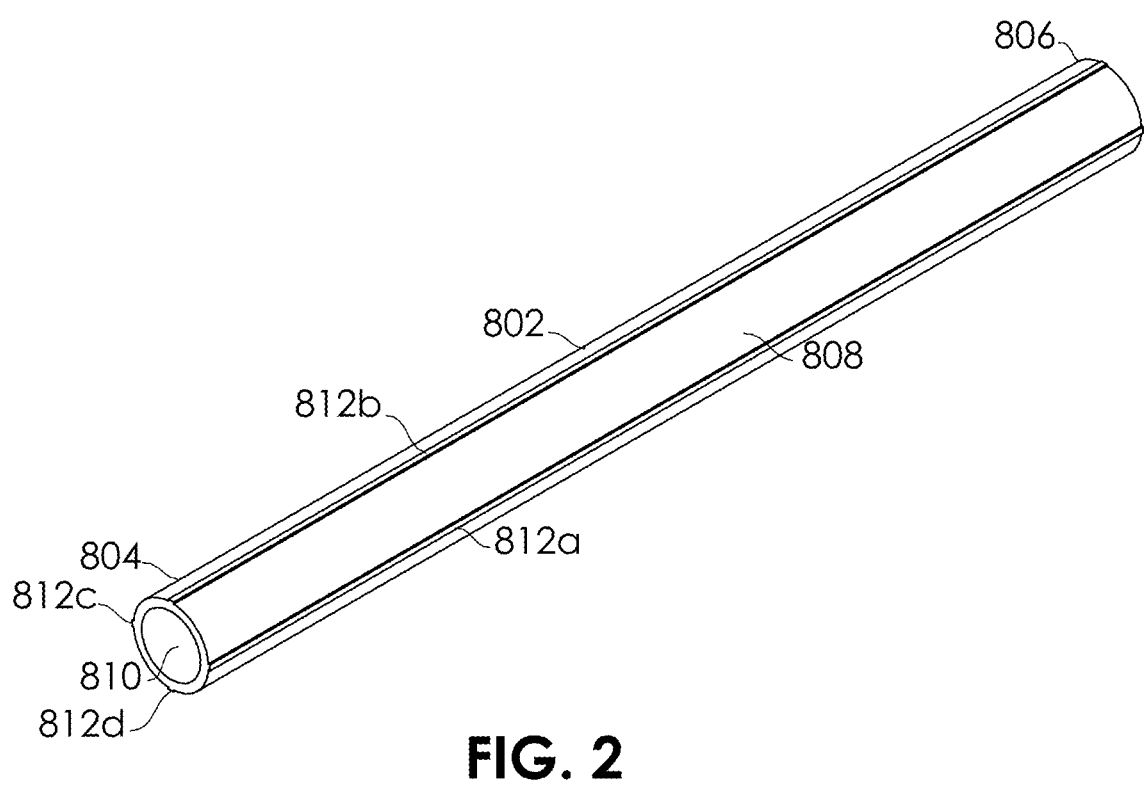
FIG. 2 is a perspective view of the tubular component of FIG. 1 having externally-applied conductive tracings.
Figure 10:
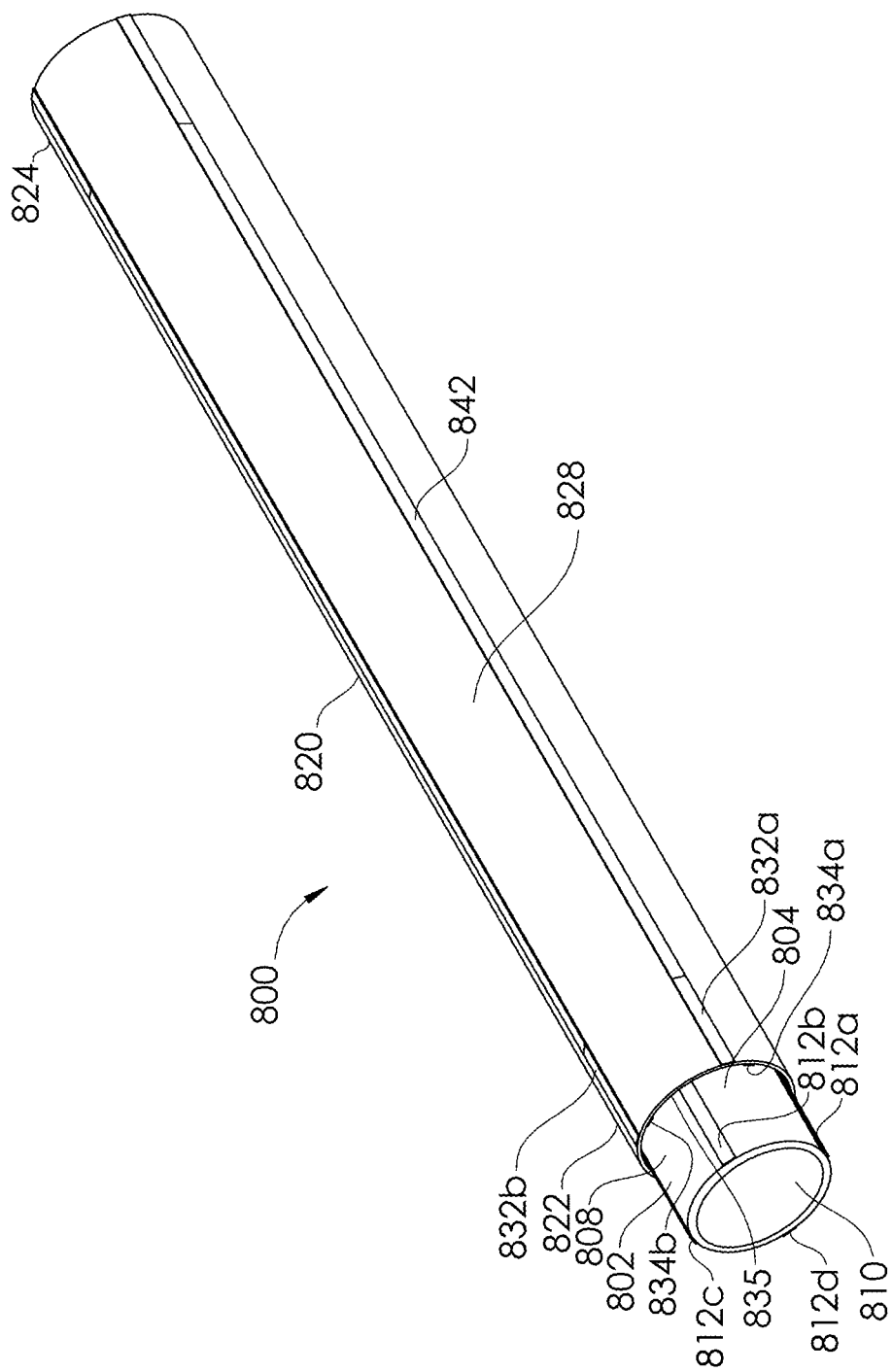
FIG. 10 is a medical device body according to an embodiment of the present disclosure which incorporates the tubular component of FIG. 3 and the membrane component of FIG. 9.

FIG. 1 illustrates an elongate member 802 having a distal end 804 and a proximal end 806 and configured as a component to construct a medical device body 800, as shown in FIG. 10. The elongate member 802 is shown in FIG. 1 as a tubular member having an outer cylindrical surface 808 and having a lumen 810 passing from the distal end 804 to the proximal end 806. However, in some embodiments, the elongate member 802 may be solid and not have a lumen 810, or alternatively, it may have two or more lumens. Additionally, in some embodiments, the elongate member 802 may have a non-circular cross-section, including, but not limited to oval, rectangular, square or polygonal. In some embodiments, the elongate member 802 may comprise a polymeric material, and in some embodiments may be formed by extrusion. FIG. 2 illustrates the elongate member 802 with one or more electrically-conductive tracings 812a-d that have been applied to the outer surface 808. The one or more electrically-conductive tracings 812a-d are shown as linear, longitudinally-extending tracings, but in other embodiments, may have curvilinear shapes, including, for example, helical paths which wind around the outer surface 808. In still other embodiments, the one or more electrically-conductive tracings 812a-d may be added to the elongate member 802 in a linear shape, as in FIG. 2, but in a secondary operation, the entire elongate member 802 or a certain length of the elongate member 802 may be heated and twisted, in order to impart a helical shape to the one or more electrically-conductive tracings 812a-d. The one or more electrically-conductive tracings 812a-d may be applied to the elongate member 802 by the use of one or more different processes. In some embodiments, the one or more electrically conductive tracings 812a-d may be deposited, painted, coated, sprayed, or sputtered. Each of the one or more electrically-conductive tracings 812a-d is configured for carrying an electrical signal along a length of the elongate member 802, in a distal direction and/or a proximal direction. The one or more electrically-conductive tracings may be applied using materials and methods described in U.S. Pat. No. 9,289,141 to Lowery et al., entitled "Apparatus and Methods for the Measurement of Cardiac Output," issued Mar. 22, 2016, which is hereby incorporated by reference in its entirety for all purposes. Furthermore, the one or more electrically-conductive tracings may be applied using materials and methods described in International Application (PCT) Publication No. WO 2016/179563 to Lowery, entitled "SYSTEMS AND METHODS FOR INTERNAL ECG ACQUISITION," published Nov. 10, 2016, the disclosure of which is incorporated by reference herein in its entirety for all purposes.

Figure 3:
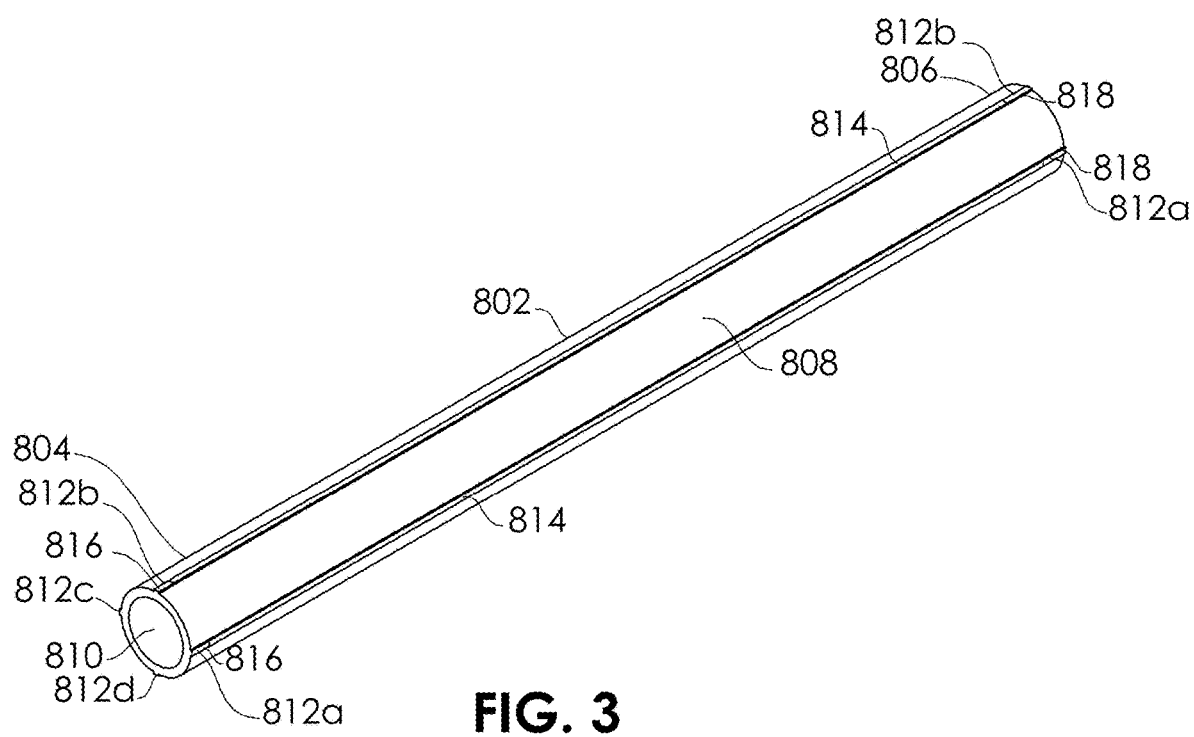
FIG. 3 is a perspective view of the tubular component of FIGS. 1 and 2, with a dielectric layer applied over at least a portion of the conductive tracings.

FIG. 3 illustrates the elongate member 802 with a dielectric layer 814 applied over at least a portion of the one or more electrically-conductive tracings 812a-d. In the embodiment illustrated in FIG. 3, the one or more electrically-conductive tracings 812a-d are covered with the dielectric layer 814 over the majority of the length of the elongate member 802, but are left uncovered at the distal end 804 and at the proximal end 806. This allows, for example, one or more sensors to be electrically connected to the uncovered portions 816 at the distal end 804 of the elongate member 802, and also allows a connector (FIGS. 13-14) to be electrically connected to uncovered portions 818 at the proximal end 806 of the elongate member 802. In some embodiments, the dielectric layer 814 only covers each of the one or more electrically-conductive tracings 812a-d, but does not substantially cover the outer surface 808 of the elongate member 802. In other embodiments, the dielectric layer 814 covers the one or more electrically-conductive tracings 812a-d, and also covers the outer surface 808 of the elongate member.

In some embodiments, the dielectric layer 814 is extruded over the one or more electrically-conductive tracings 812a-d and the outer surface 808 in an over-extrusion process. Subsequent to the over-extrusion process, the dielectric layer 814 may be removed from the one or more electrically-conductive tracings 812a-d only at the uncovered portions 816, 818. Alternatively, a dip coating process may be used to apply the dielectric layer 814. The electrically-conductive tracings 812a-d may be marked prior to dipping at the distal and proximal ends 804, 806 so that after dipping, the masking can be removed, leaving uncovered portions 816, 818. In some embodiments, the dielectric layer 814 may comprise polyimide, adhesive, such as UV curable adhesive, silicone adhesive, or polyurethane adhesive, epoxies, or shrink tubing, such as polyethylene shrink tubing, PTFE shrink tubing, or polyester shrink tubing.

Figure 4:
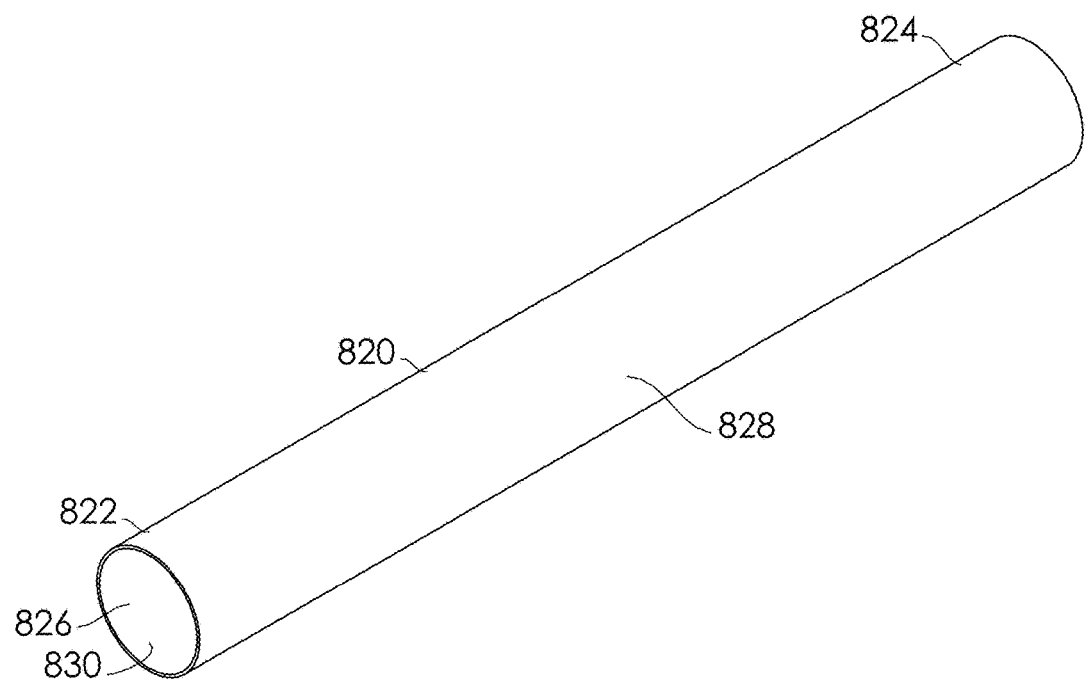
FIG. 4 is a perspective view of a membrane component of a medical device.

FIG. 4 illustrates a tubular member 820 configured as a component to construct the medical device body 800 (FIG. 10). In some embodiments, the tubular member 820 will be applied over the elongate member 802. The tubular member 820 has a distal end 822 and a proximal end 824 and has a lumen 826 extending therethrough. The tubular member 820 includes an outer cylindrical surface 828 and an inner cylindrical surface 830. Though in FIG. 4 the tubular member 820 is illustrated as having a single lumen, in other embodiments, the tubular member may comprise two or more lumens. Though illustrated with a circular cross-section in FIG. 4, in other embodiments, the tubular member 820 may have a non-circular cross-section, including, but not limited to oval, rectangular, square or polygonal. In some embodiments, the tubular member 820 may comprise a polymeric material, and in some embodiments may be formed by extrusion.

Figure 5A:
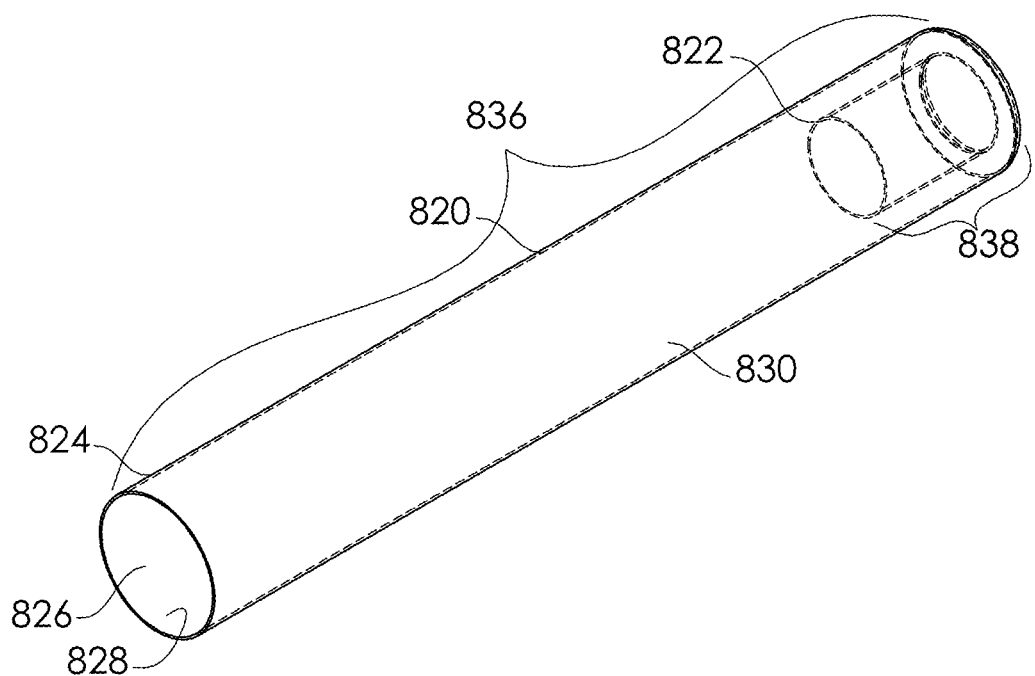
FIG. 5A is a perspective view of the membrane component of FIG. 4 after it has been partially everted.
Figure 6:
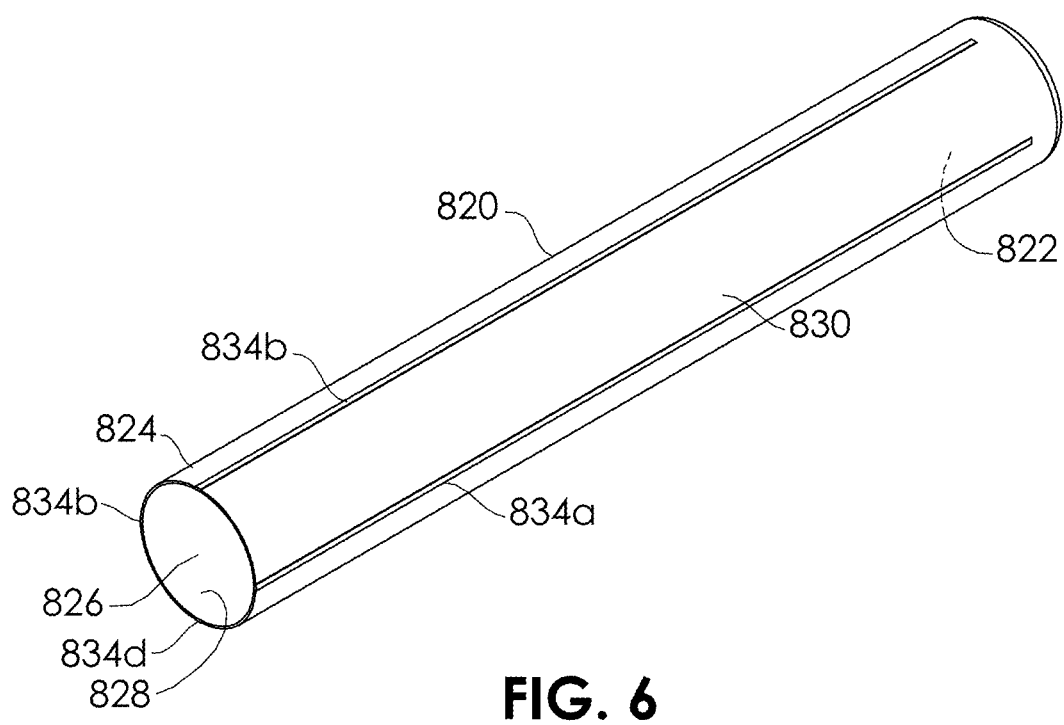
FIG. 6 is a perspective of the everted membrane component of FIGS. 5A and 5B having conductive tracings applied to the everted, externally-facing interior surface.
Figure 5B:
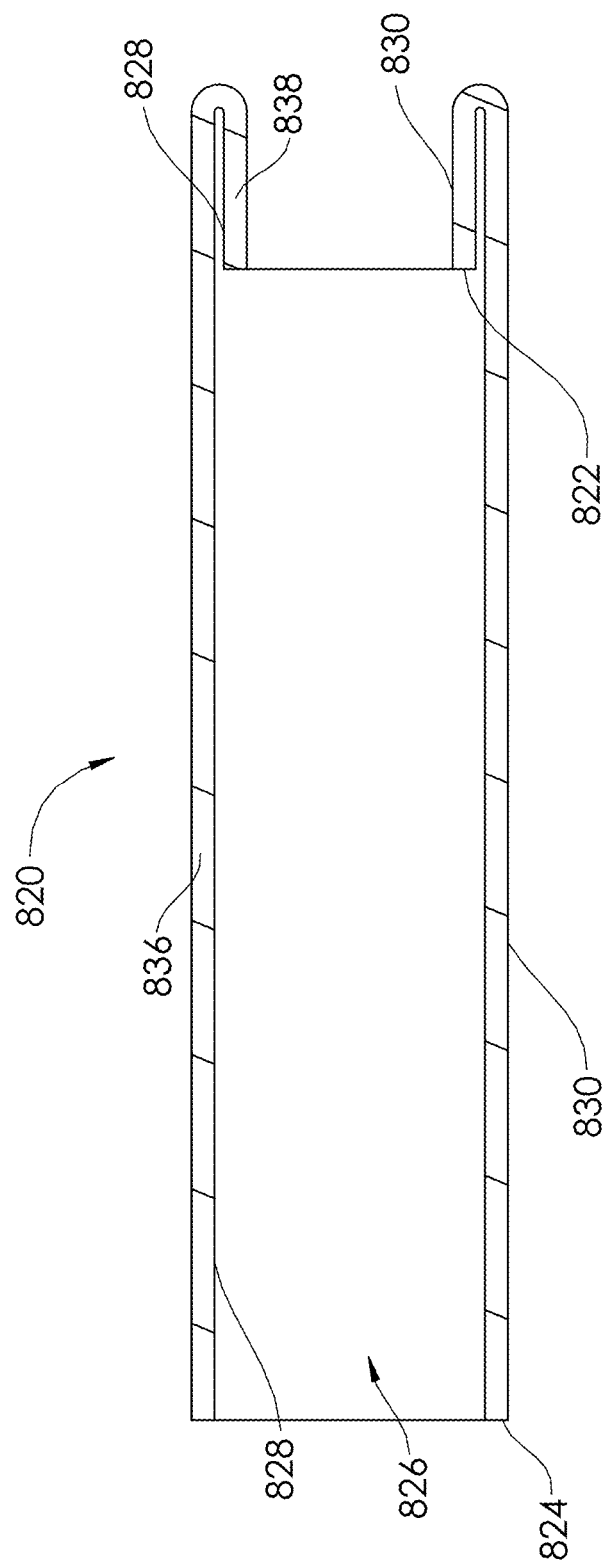
FIG. 5B is a sectional view of the everted membrane component of FIG. 5A.
Figure 7:
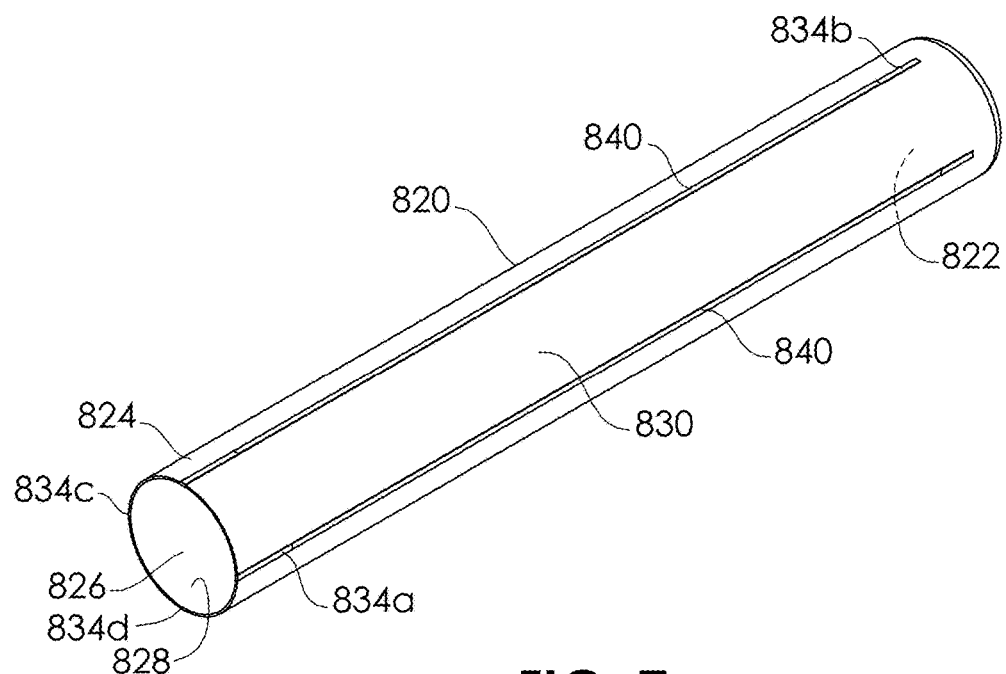
FIG. 7 is the everted membrane component of FIG. 6 with a dielectric layer applied over at least a portion of the conductive tracings.

In some applications, a relatively large number of electrically-conductive tracings may be required to be carried on the medical device body 800, and so an everting process is utilized with the tubular member 820 so that one or more electrically-conductive tracings 832, 834 (FIG. 8) may be applied to both the outer cylindrical surface 828 and the inner cylindrical surface 830. In FIGS. 5A and 5B, the tubular member 820 is at least partially everted by folding one end 824 over the outer diameter of the tubular member 820 so that at least a portion of the outer surface 828 becomes internally-facing. For example, in FIGS. 5A and 5B, an everted portion 836 includes the now externally-facing inner surface 830 and the now internally-facing outer surface 828. A non-everted portion 838, which is within a partial length of the everted portion 836, includes a still internally-facing inner surface 830 and a still externally-facing outer surface 828 (FIG. 5B). In FIG. 6, one or more electrically-conductive tracings 834a-d are applied to the externally-facing inner surface 830 of the everted portion 836 of the tubular member 820 by any of the methods disclosed herein. In FIG. 7, a dielectric layer 840 is applied over at least a portion of the one or more electrically-conductive tracings 834*a-d*. In the embodiment illustrated in FIG. 7, the one or more electrically-conductive tracings 834*a-d* are covered with the dielectric layer 840 over the majority of the length of the elongate member 802, but may be left uncovered at the distal end 804 and at the proximal end 806, as described above in relation to the elongate member 802. The eversion process may be aided with the use of a rigid tube that is placed over the tubular member 820 up to the point where eversion is to take place. The inner diameter of the rigid tube may be slightly larger than the outer diameter of the tubular member 820 and be of a relatively stiff material with thin walls. For example, thin wall stainless steel or PEEK tubes may be utilized.

Figure 8:
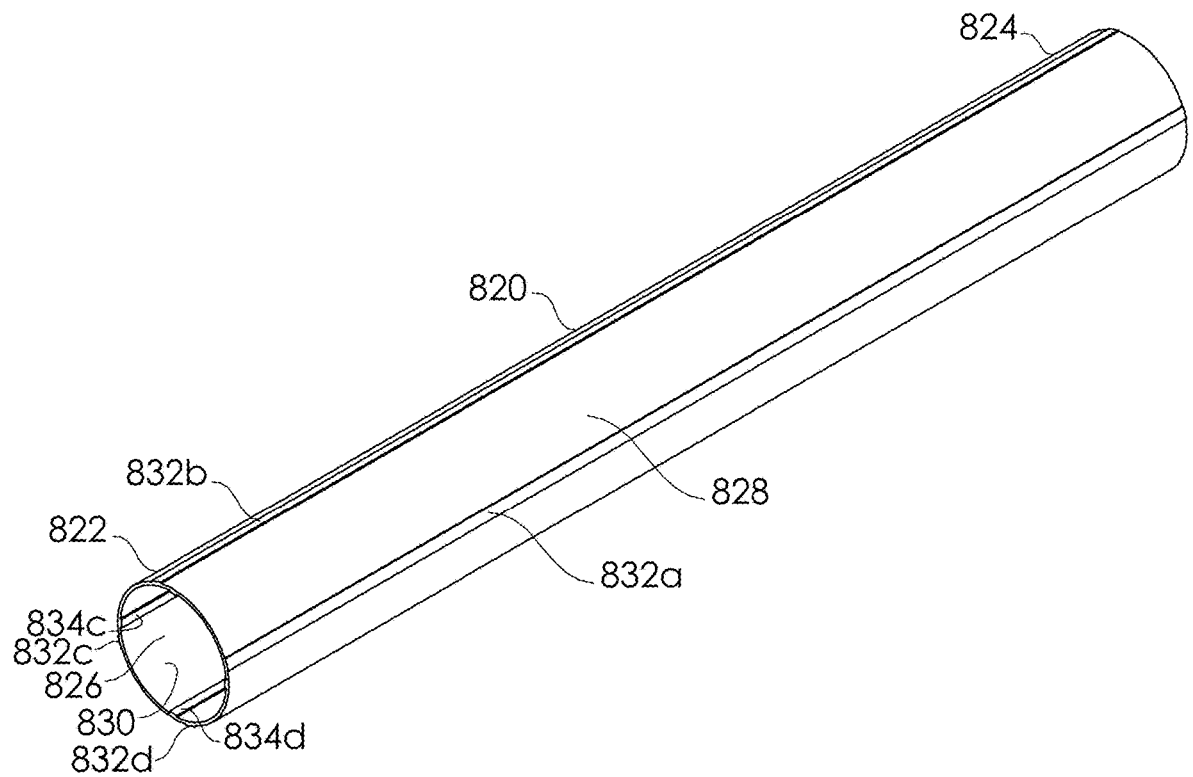
FIG. 8 is the membrane component of FIGS. 4-7 after having been reverted back to its original tubular state, and with an additional conductive tracings applied to its exterior surface.
Figure 9:
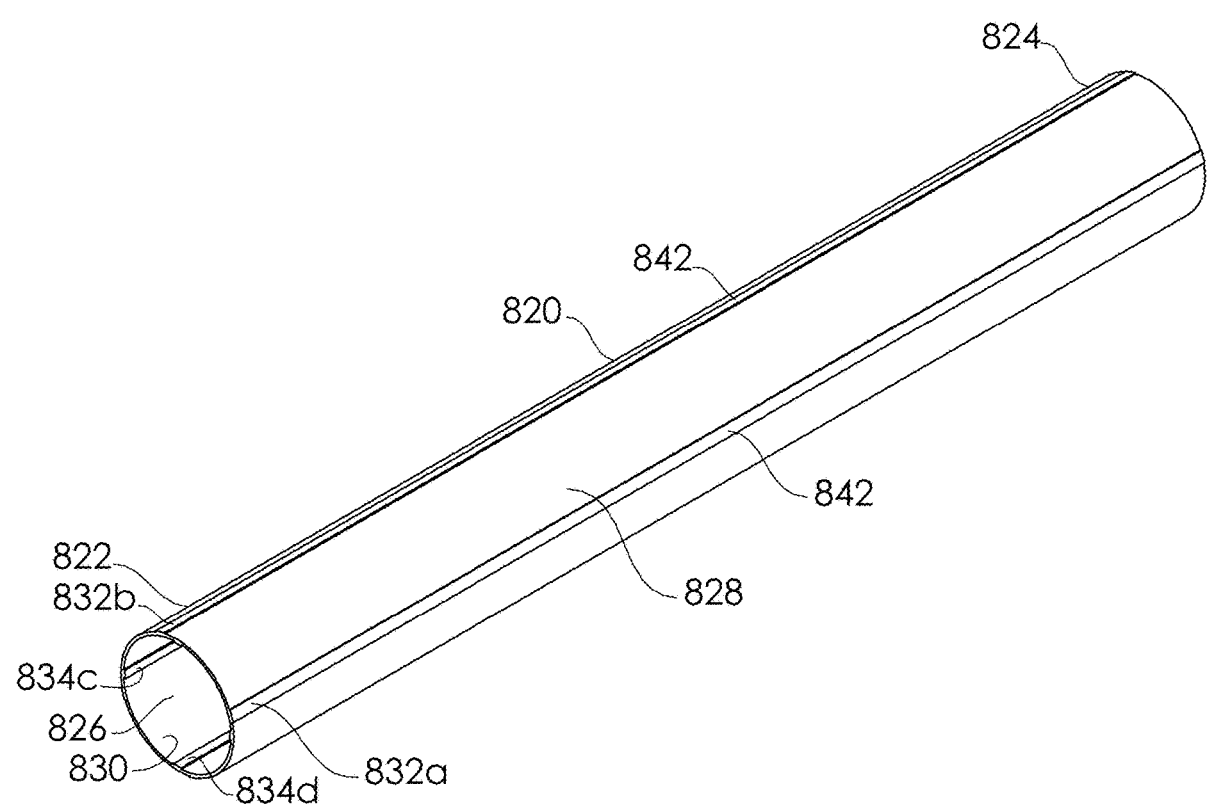
FIG. 9 is the membrane component of FIG. 8 with a dielectric layer applied over at least a portion of the external conductive tracings.

In FIG. 8, the tubular member 820 is reverted after the one or more electrically-conductive tracings 834*a-d* and the dielectric layer 840 are applied. The one or more electrically-conductive tracings 834*a-d* are now located on the again fully internally-facing inner surface 830. Throughout both the original, everted, and reverted conditions, the reference to the lumen 826 has remained constant, as it refers to the space in the center of the structure of the tubular member 820. One or more electrically-conductive tracings 832*a-d* are now applied to the (again) externally-facing outer surface 828. The methods and materials related to the one or more electrically-conductive tracings 832*a-d* may be the same as those described in relation to the one or more electrically-conductive tracings 834*a-d*. In FIG. 9, a dielectric layer 842 may be applied to the electrically-conductive tracings 832*a-d* in order to electrically isolate them. The methods and materials related to the dielectric layer 842 may be the same as those described in relation to the dielectric layer 814.

FIG. 10 illustrates a medical device body 800 comprising the tubular member 820 secured over the elongate member 802. In some embodiments, the tubular member 820 may be secured to the elongate member 802 with adhesive or epoxy, or may be heat-fused to the elongate member 802. For example, the adhesive or epoxy may be placed in an annular space 835 between the tubular member 820 and the elongate member 802. In some embodiments, the tubular member 820 is constructed from slightly-stretched (in radial direction) heat-shrinkable tubing, and thus may be shrunk over the elongate member 802. The resulting medical device body 800 comprises three layers of electrically-conductive tracings 812*a-d*, 834*a-d*, 832*a-d*, all electrically isolated from each other. The electrical isolation between the electrically-conductive tracings 832*a-d* and the electrically-conductive tracings 834*a-d* is provided by the electrically-insulative material (e.g., polymer) of the tubular member 820. The electrical isolation between the electrically-conductive tracings 812*a-d* and the electrically-conductive tracings 834*a-d* may be provided by either the dielectric layer 814, the dielectric layer 840, the adhesive or epoxy between the tubular member 820 and the elongate member 802, or any combination thereof. It should be noted that one of either the dielectric layer 814 or the dielectric layer 840 may be omitted, as the one or more electrically conductive tracings 812*a-d* can be electrically isolated from the electrically-conductive tracings 834*a-d* with just a single dielectric layer. In other embodiments, the dielectric layer 840 may be applied after the tubular member 820 is reverted (FIG. 8), by injecting the dielectric material 840 in liquid form, for example, with a solvent, through the lumen 826 of the tubular member 820, thus covering the electrically-conductive tracings 834*a-d* and the exposed cylindrical surface 830. The dielectric layer 842 may even be applied over the electrically-conductive tracings 832*a-d* in this same manner, by applying the electrically-conductive tracings 832*a-d*, everting the tubular member 820, and then injecting the dielectric material 842 in liquid form, through the everted tubular member 820. Thus, a flexible device having a large number of conductors can be constructed without a large increase in overall diameter. The electrically-conductive tracings 832*a-d*, 812*a-d* are externally-facing over their entire lengths and the electrically-conductive tracings 834*a-d* are internally facing over their entire lengths.

Again, although depicted in straight line patterns, any of the electrically-conductive tracings 834*a-d*, 832*a-d*, 812*a-d* may have non-linear shapes, such as helices or serpentine paths. These non-linear paths may add other favorable characteristics. For example, a helical or serpentine path may allow greater flexibility of the medical device body 800 or any of its elements. These shapes and other non-linear shapes may also aid the packing of larger number of traces and/or increasing (or decreasing) the flexibility of the medical device body 800, as desired. As shown in FIG. 10, the circumferential orientation of each of the one or more electrically-conductive tracings 812*a-d*, 834*a-d*, 832*a-d* can be purposely varied relative to each other so that no or few tracings overlap, which can help lower the overall profile/diameter of the medical device body 800 and increase flexibility of the medical device body 800. Though the medical device body 800 is described in FIG. 10, in other embodiments, the tubular member 820 after the operations described in FIG. 9 may also be used as a complete medical device body (i.e., if the elongate member 802 is not required.

In embodiments wherein the tubular member 820 and the elongate member 802 are both non-circular, they may both have a similar contour so that they fit within each other efficiently. For example, the lumen 826 of the tubular member may have a similar contour as the outer cylindrical surface 808 of the elongate member, and a maximum transverse dimension of the lumen 826 may be about the same size or slightly larger than a maximum transverse dimension of the outer cylindrical surface 808. Likewise, a minimum transverse dimension of the lumen 826 may be about the same size or slightly larger than a minimum transverse dimension of the outer cylindrical surface 808.

Figure 11:
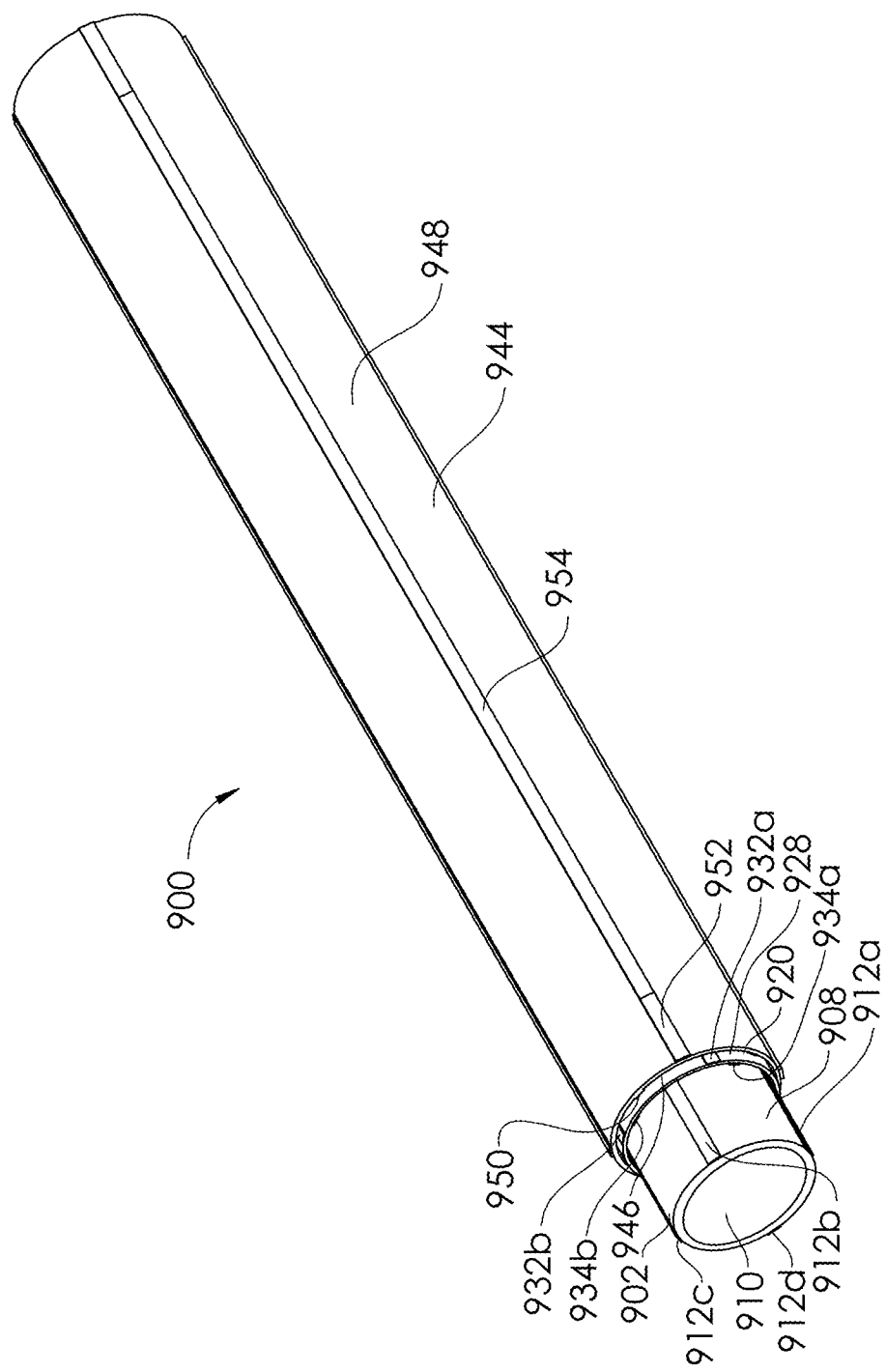
FIG. 11 is a medical device body according to another embodiment of the present disclosure which incorporates two membrane components.

FIG. 11 illustrates an alternative embodiment of a medical device body 900 comprising an elongate member 902 having a lumen 910, a first tubular member 920, and a second tubular member 944. The elongate member 902 and the first tubular member 920 are produced and assembled in the same manner as the elongate member 802 and the tubular member 820 of the medical device body 800 of FIGS. 1-10. The elongate member 902 includes one or more electrically-conductive tracings 912*a-d* applied to its outer surface 908, and the first tubular member 920 has one or more electrically-conductive tracings 934*a*-dapplied to its inner surface (not shown) (934*c-d* not shown) and one or more electrically-conductive tracings 932*a-d* applied to its outer surface 928 (932*c-d* not shown). As in the tubular member 820 of FIG. 10, the one or more electrically-conductive tracings 934*a-d* applied to its inner surface are applied with the first tubular member 920 everted. The second tubular member 944 includes an inner surface 946 and an outer surface 948. One or more electrically-conductive tracings 950 are applied on the inner surface 946 (e.g., with the second tubular member 944 everted), and one or more electrically-conductive tracings 952 are applied on the outer surface 948. A dielectric coating (not shown) may be applied over the one or more electrically-conductive tracings 950, and a dielectric coating 954 may be allied over the one or more electrically-conductive tracings 950. The second tubular member 944 is secured over the first tubular member 920 by any of the manners described in relation to the tubular member 820 and the elongate member 802. The resulting medical device body 900 thus has five separate layers of one or more electrically-conductive tracings 912, 934, 932, 950, 952. The tracings can be varied in shape, pattern, and materials as described in relation to the medical device body 800 of FIGS. 1-10. The materials of the one or more electrically-conductive tracings 912, 934, 932, 950, 952 and the dielectric coatings may be the same as those described in relation to the medical device body 800 of FIGS. 1-10. A final coating of a lubricious material such as silicone or PTFE may be applied over the medical device body 800, 900, 1000, in order to facilitate movement through body lumens or ducts.

Figure 12:
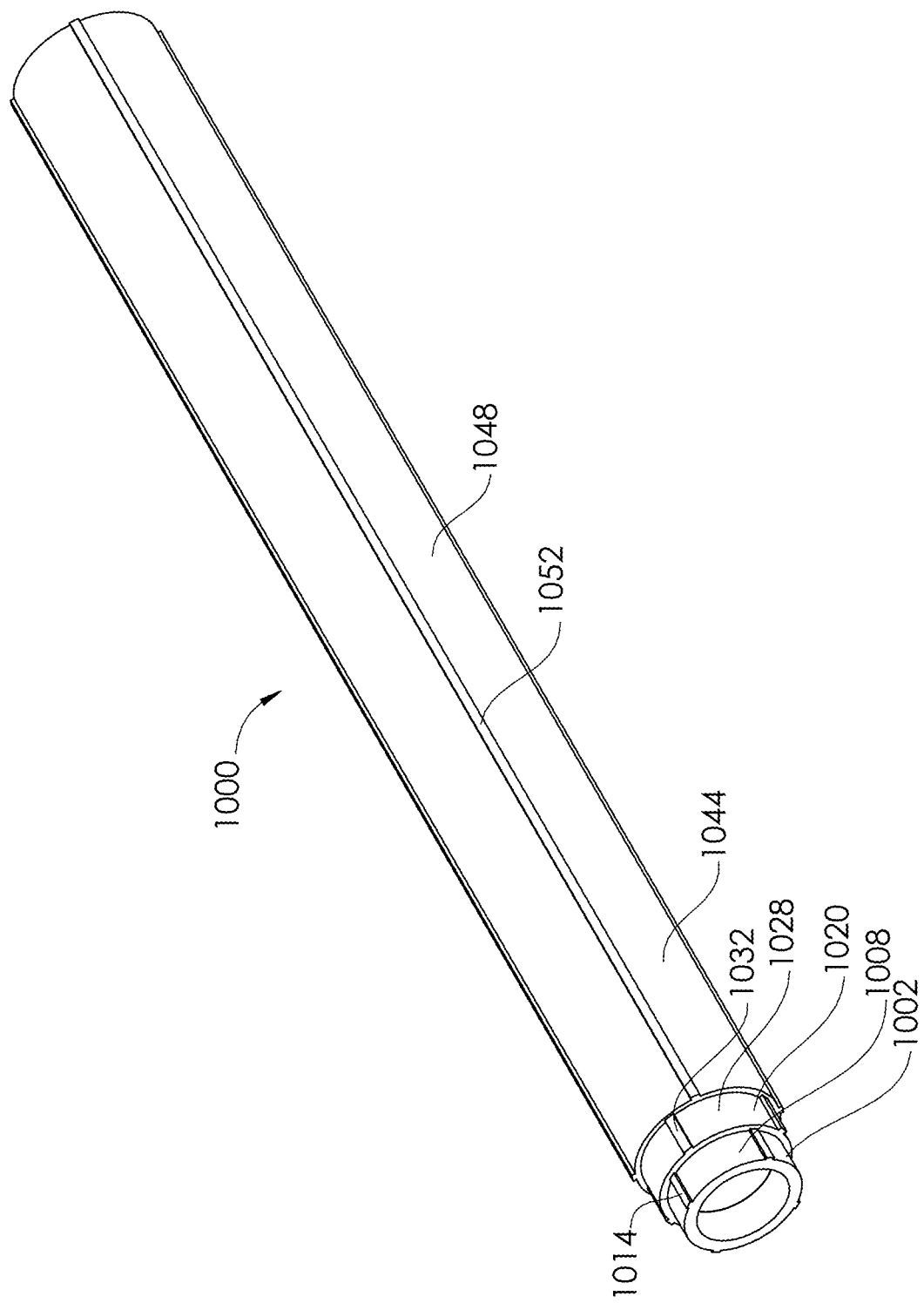
FIG. 12 is a medical device body according to another embodiment of the present disclosure.

FIG. 12 illustrates an alternative embodiment of a medical device body 1000 comprising an elongate member 1002, a first tubular member 1020, and a second tubular member 1044, each having one or more electrically-conductive tracings 1014, 1032, 1052 applied onto their respective outer surfaces 1008, 1028, 1048. Instead of attaching separate components, the first tubular member 1020 is over-extruded over the elongate member 1002 and electrically-conductive tracing 1014 creating the outer surface 1028, and the second tubular member 1044 is over-extruded over the combined elongate member 1002, electrically-conductive tracing 1014, first tubular member 1020, and electrically-conductive tracing 1032, creating the outer surface 1048. Following this, one or more electrically conductive tracings 1052 are applied to the outer surface 1048 of the over-extruded second tubular member 1044. Alternatively, the first tubular member 1020 and a second tubular member 1044 may be applied by dip coating, instead of by an extrusion process.

Figure 13:
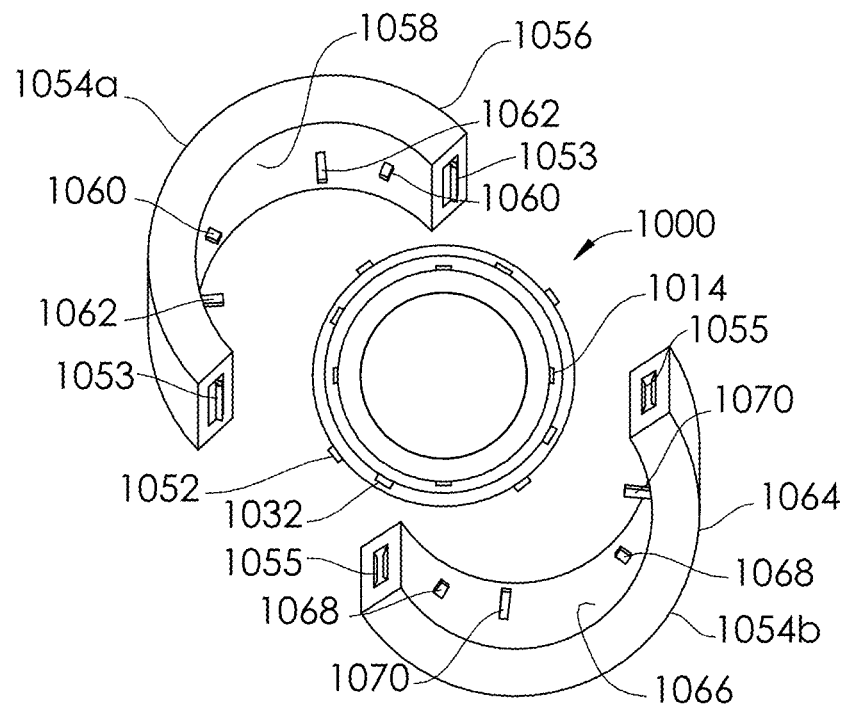
FIG. 13 is perspective view of a connector being attached to the medical device body of FIG. 12, according to an embodiment of the present disclosure.
Figure 14:
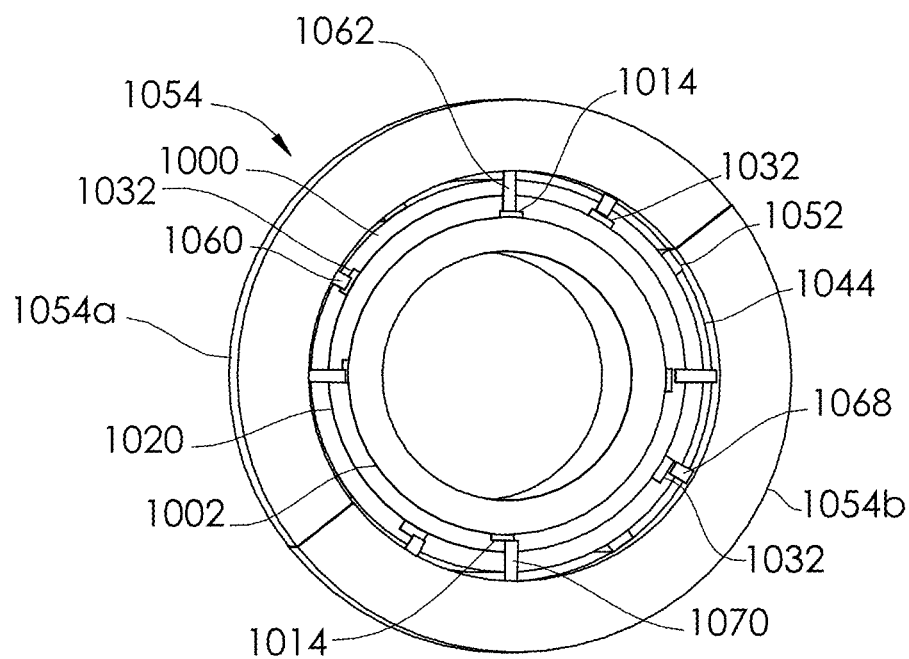
FIG. 14 is a cross-sectional view of the connector and the medical device body coupled together.
Figure 15:
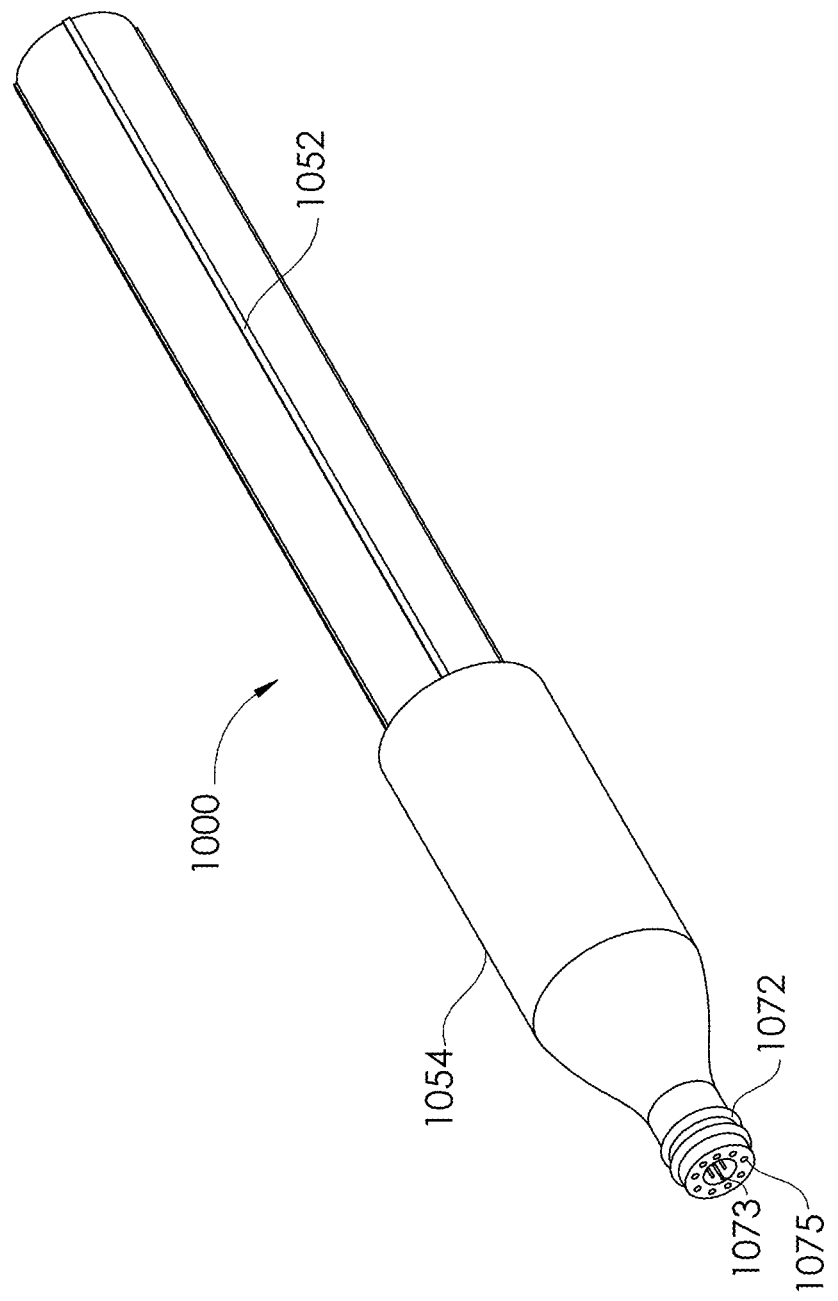
FIG. 15 is a perspective view of the connector and the medical device body coupled together.

FIGS. 13-15 illustrate a split connector 1054 comprising a first half 1054a and a second half 1054b, configured to couple to the medical device body 1000 of FIG. 12. The first half 1054a includes a housing 1056, a conductive plate 1058, one or more first conductive pins 1060, and one or more conductive pins 1062. The second half 1054b includes a housing 1064, a conductive plate 1066, one or more first conductive pins 1068, and one or more conductive pins 1070. The first half 1054a is configured to close and secure to the second half 1054b while making the following electrical connections when the halves 1054a, 1054b are closed and secured by tabs 1053 which snap into slots 1055: the conductive plates 1058, 1066 are configured to contact the one or more electrically-conductive tracings 1052 of the outer surface 1048 of the second tubular member 1044; the one or more conductive pins 1060,1068 are configured to contact the one or more conductive tracings 1032 of the first tubular member 1020; and the one or more conductive pins 1062, 1070 are configured to contact the one or more conductive tracings 1014 of the elongate member 1002. In some embodiments, the conductive plates 1058, 1066 are configured to apply normal forces to the outer surfaces of the one or more conductive tracings 1052 in order to make the electrical contacts. The one or more conductive pins 1060, 1068 are configured to penetrate the material of the second tubular member 1044 and to apply normal forces on the outer surfaces of the one or more conductive tracings 1032 in order to make the electrical contacts. The one or more conductive pins 1062, 1070 are configured to penetrate the material of both the second tubular member 1044 and the first tubular member 1020 and to apply normal forces on the outer surfaces of the one or more conductive tracings 1014 in order to make the electrical contacts. The connector 1054 is shown connected to the medical device body 1000 in FIG. 15. The connector 1054 includes an interface 1072 for coupling to a control console of the medical device. The conductive plates, 1058, 1066, and conductive pins 1060, 1062, 1068, 1070 are each electrically coupled (e.g., by solder) to the interface 1072 (e.g., by insulated conductors/wires). The interface 1072 may comprise a multi-pin 1073 or multi-port 1075 connection (or a combination thereof) in order to couple several different electrical connections and thus allow for several parallel signal pathways. Alternatively, or in conjunction with the tabs 1053 and slots 1055, the halves 1054a, 1054b may be attached by other means, including adhesive, epoxy, or welding.

In an alternative embodiment, the holes made by the penetration of the conductive pins 1060, 1062, 1068, 1070 through the material of the second tubular member 1044 and the first tubular member 1020, can instead be predrilled, pre-punched or pre-punctured. The conductive pins 1060, 1062, 1068, 1070 can then be placed through the holes. Alternatively, a connection without pins can be used, with the holes instead filled with conductive material (solder, etc.) to the surface.

Figure 16:
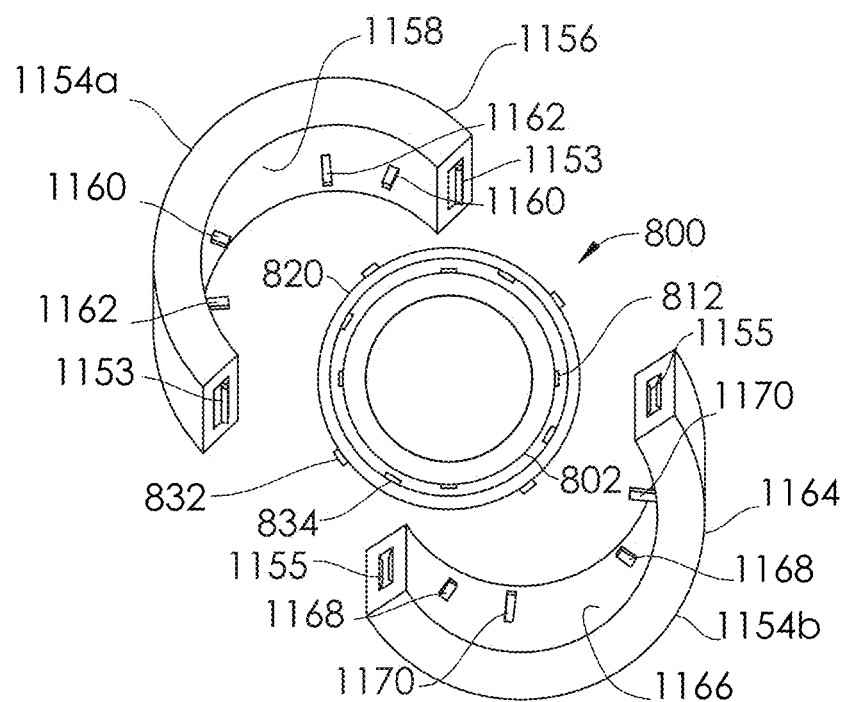
FIG. 16 is perspective view of a connector being attached to the medical device body of FIG. 10, according to an embodiment of the present disclosure.
Figure 17:
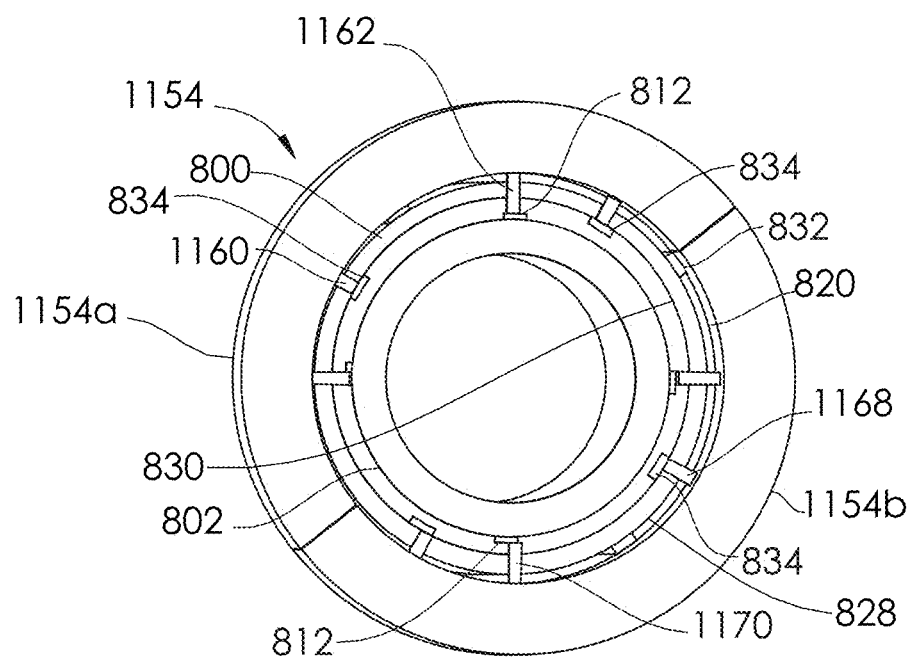
FIG. 17 is a cross-sectional view of the connector and the medical device body coupled together.
Figure 18:
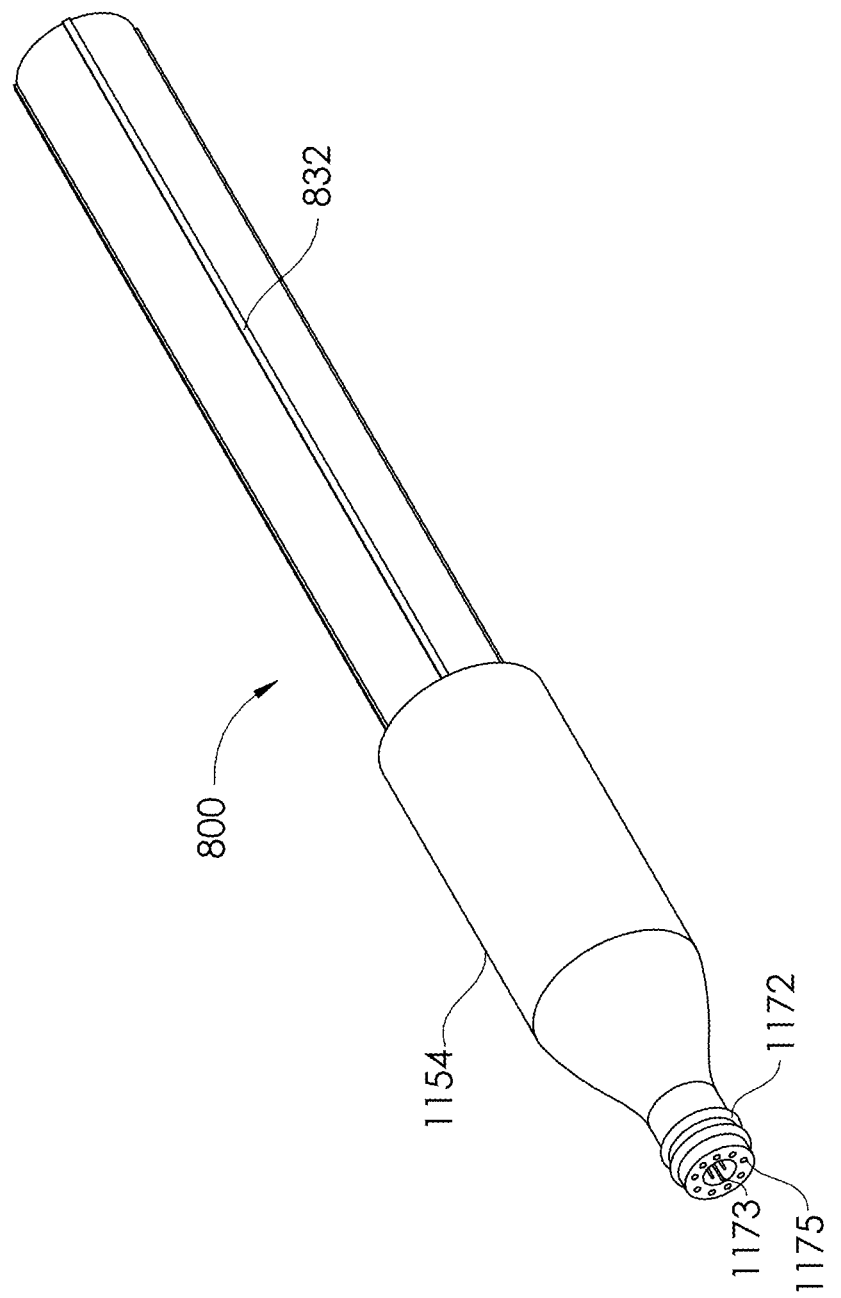
FIG. 18 is a perspective view of the connector and the medical device body coupled together.

FIGS. 16-18 illustrate a split connector 1154 comprising a first half 1154a and a second half 1154b, configured to couple to the medical device body 800 of FIG. 10. The first half 1154a includes a housing 1156, a conductive plate 1158, one or more first conductive pins 1160, and one or more conductive pins 1162. The second half 1154b includes a housing 1164, a conductive plate 1166, one or more first conductive pins 1168, and one or more conductive pins 1170. The first half 1154a is configured to close and secure to the second half 1154b while making the following electrical connections when the halves 1154a, 1154b are closed and secured by tabs 1153 which snap into slots 1155: the conductive plates 1158, 1166 are configured to contact the one or more electrically-conductive tracings 832 of the outer cylindrical surface 828 of the tubular member 820; the one or more conductive pins 1160, 1168 are configured to contact the one or more conductive tracings 834 of the inner cylindrical surface 830 of the tubular member 820; and the one or more conductive pins 1162, 1170 are configured to contact the one or more conductive tracings 812 of the elongate member 802. In some embodiments, the conductive plates 1158, 1166 are configured to apply normal forces to the outer surfaces of the one or more conductive tracings 832 in order to make the electrical contacts. The one or more conductive pins 1160, 1168 are configured to penetrate the material of the tubular member 820 and to contact the back (externally-facing) sides of the one or more conductive tracings 834 in order to make the electrical contacts. The one or more conductive pins 1162, 1170 are configured to penetrate the material of the tubular member 820 and to apply normal forces on the outer surfaces of the one or more conductive tracings 812 of the elongate member 802 in order to make the electrical contacts. The connector 1154 is shown connected to the medical device body 800 in FIG. 18. The connector 1154 includes an interface 1172 for coupling to a control console of the medical device. The conductive plates, 1158, 1166, and conductive pins 1160, 1162, 1168, 1170 are each electrically coupled (e.g., by solder) to the interface 1172 (e.g., by insulated conductors/wires). The interface 1172 may comprise a multi-pin 1173 or multi-port 1175 connection (or a combination thereof) in order to couple several different electrical connections and thus allow for several parallel signal pathways. Alternatively, or in conjunction with the tabs 1153 and slots 1155, the halves 1154a, 1154b may be attached by other means, including adhesive, epoxy, or welding.

The polymeric materials described herein, for example, in relation to the elongate shafts/tubing, may include polyvinyl chloride, nylon, polyurethane, or polyether block amide. The dielectric materials described herein may include polyimide, adhesive, epoxy, polyethylene shrink tubing, or polyester shrink tubing.

Figure 19:
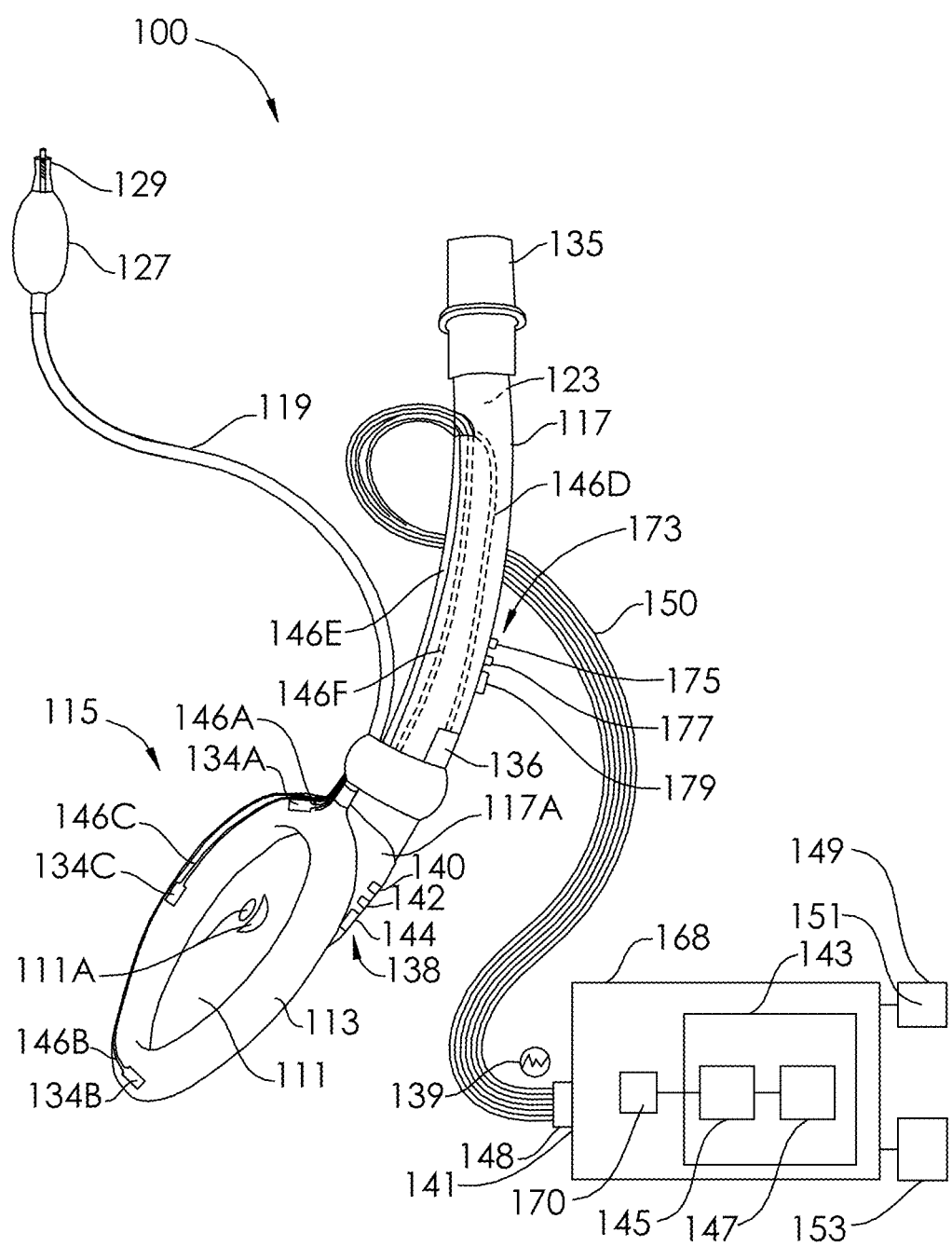
FIG. 19 is a system for cardiovascular sensing including a laryngeal mask, according to an embodiment of the present disclosure.

A large range of medical devices having diagnostic and/or therapeutic functionalities may be manufactured using medical device bodies 800, 1000 having features described herein. Some particular examples follow. A system for measurement of cardiovascular parameters 100 is illustrated in FIG. 19. The system for measurement of cardiovascular parameters 100 includes a sensing device which is a laryngeal mask or laryngeal airway (LMA) 115 having sensing capabilities. One method to maintain an oral airway during anesthetic management or mechanical ventilation, utilizes a laryngoscope for endotracheal intubation. Alternatively, a laryngeal mask airway can be inserted into the larynx. A laryngeal mask or laryngeal mask airway (LMA) 115, as shown in FIG. 19, comprises an oval mask body 111 and a hollow cuff 113 which engages the periphery of the mask body 111 and has a ring-shaped luminal area. The hollow cuff 113 may follow the oval shape of the mask body 111. A respiratory tube 117 is connected to a tube connecting portion 117A on the outside surface of the mask body 111. The respiration is performed through the holes 111A which are formed in the mask body 111, and through an elongate passageway 123 in the respiratory tube 117. A fitting 135 is sealingly attached to the respiratory tube 117 and is configured for coupling to mechanical ventilation equipment. The fitting 135 is configured to couple to a respiratory or other oxygen or air delivery apparatus, for delivering oxygen and other gases, which may in some cases include an anesthetic, through the respiratory passageway 123 and out the holes 111A and then into the patient's lungs. An inflation tube 119, fluidly coupled to the cuff 113, is configured for injecting air into the cuff 113. A valve 127 carried in fluid communication with the inflation tube 119 may be used to maintain the pressurized air within the cuff 113. In some embodiments, the valve 127 may be a one-way valve (open or closed). In some embodiments, the valve 127 may be a pinch valve, which is normally in a closed condition be may be pinched to allow air to enter or exit the inflation tube 119. In some embodiments, the valve 127 may be a luer-activated valve which allows air to enter of exit the inflation tube 119 when a luer or a syringe (not shown) is attached to a luer connector 129 at the end of the inflation tube 119. Prior to insertion of the LMA 115, an anesthesiologist or other medical professional deflates the cuff 113 by extracting air therefrom. Once the anesthesiologist or other medical professional inserts the LMA 115 into a patient's larynx, he or she then inflates the cuff 113 by introducing air therein. In this manner, an airway is maintained by covering the larynx with the LMA 115.

The LMA 115 incorporates one or more sensors, which may include one or more cuff-based sensors 134 (134A, 134B, 134C), and one or more tube-based sensors 136. The number of sensors 134, 136 on the cuff 113 and/or the tube 117 (which may include the tube connecting portion 117A) may be varied in different embodiments. In addition, an optical sensor 138 (for example, a pulsed oximetry device) having at least two light emitting sources 140, 142 and one light detector 144, is mounted on the mask body 111 and/or the tube 117/tube connecting portion 117A (shown on the tube connecting portion 117A in FIG. 19). The optical sensor 138 may even be located on the cuff 113, for example, a rearwardly-facing portion of the cuff 113 that does not directly engage tissue of the body lumen when the cuff 113 is inflated. The optical sensor 138 is configured to obtain plethysmographic data when it is positioned in spaced relation with tissue, for example, in a non-contact arrangement with an inner wall of a body lumen. The sensors 134, 136 may comprise electrodes and utilize bio-impedance to generate waveforms representative of the flow of blood through the carotid arteries. Examples of bioelectrical impedance analysis of blood flow using electrode sensors arrayed within body lumens, at least some of the sensors contacting mucosal tissue can be found in U.S. Pat. No. 5,791,349, issued on Aug. 11, 1998, and entitled "APPARATUS AND METHOD OF BIOELECTRICAL IMPEDANCE ANALYSIS OF BLOOD FLOW," U.S. Pat. No. 5,782,774, issued on Jul. 21, 1998, and entitled "APPARATUS AND METHOD OF BIOELECTRICAL IMPEDANCE ANALYSIS OF BLOOD FLOW," U.S. Pat. No. 6,095,987, issued on Aug. 1, 2000, and entitled "APPARATUS AND METHODS OF BIOELECTRICAL IMPEDANCE ANALYSIS OF BLOOD FLOW," U.S. Pat. No. 6,292,689, issued on Sep. 18, 2001, and entitled "APPARATUS AND METHODS OF BIOELECTRICAL IMPEDANCE ANALYSIS OF BLOOD FLOW," all of which are hereby incorporated by reference in their entirety for all purposes. Electrodes may comprise a coil, a copper band, a gold band, or a silver band. Electrodes may be soldered, welded, crimped, or attached via other mechanical methods.

The sensors 134, 136 are electrically coupled to conductive traces 146A, 146B, 146C, all of which may be painted, sprayed, or printed on the cuff 113, the tube 117, or even the inflation tube 119 by any of the methods and using any of the materials described herein, or by the methods described in international publication number WO2016/179563, published on Nov. 10, 2016, and entitled "SYSTEMS AND METHODS FOR INTERNAL ECG ACQUISITION," and described in U.S. Pat. No. 9,289,141, issued on Mar. 22, 2016, and entitled "APPARATUS AND METHODS FOR THE MEASUREMENT OF CARDIAC OUTPUT." As shown in FIG. 19, the conductive traces 146A, 146B, 146C are applied onto the cuff 113. Additional conductive traces 146D, 146E, 146F are applied on and within the tube 117 using the materials and methods of FIGS. 1-12. The conductive traces 146A, 146B, 146C, 146D, 146E, 146F connect the sensors 134, 136 (e.g., electrodes), and optical sensor 138 to a multi-contact connector 148 via an extension 150 which may contain conductive wires or traces. Conductive trace 146D within a portion of the tube 117 connects sensor 136 to the extension 150. Conductive trace 146E within a portion of the tube 117 connects optical sensor 138 to the extension 150. Conductive trace 146F on an external portion of the tube 117 connects conductive trace 146B to the extension 150. Electrical connections between components may be created using solder or mechanical attachment.

The connector 148 may be configured to be coupled to an input 141 of a console 168 and is configured to carry signals 139 from the one or more sensors 134, 136 and first optical sensor 138 to the console 168. In some embodiments, the console 168 may include an analog-to-digital converter 170 through which the one or more signals 139 are converted. In some embodiments, the signals 139 may be multiplexed. The one or more signals 139 may enter a processor 143 provided by the console 168. The processor 143 may include one or more amplifiers 145 for amplifying the signal 139 and one or more filters 147 for filtering the signal 139. A display 149 is configured to display a resulting graphic representation 151. The graphic representation 151 may simply be a parameter value or a table of values, or may actually be a graph of data, for example a plethysmograph. The display 149 may be built in to the console 168 or may be separate. The display 149 may be directly connected to the console 168 or may be remote and communicate wirelessly. The console 168 may include an interface 153 which allows a user to control and/or communicate with the console 168 or the system for measurement of cardiovascular parameters 100 in general. The interface 153 may even allow a user to control or communicate with the LMA 115, for example, if the LMA 115 incorporates an internal microprocessor, which may be carried on a flex circuit. The interface 153 may be a touch screen, a keyboard, an audio communication system (e.g., voice-activated), and may incorporate a graphic user interface (GUI). The processor 143 is configured to calculate one or more value, including but not limited to, stroke volume, heart rate, and $SpO_2$ from photoplethysmographic data provided by the first optical sensor 138 and the electrocardiogram signal and blood flow information provided by the first, second, and third sensors 134A, 134B, 134C. The emitters 140, 142 and detector 144 of the first optical sensor 138 function as a pulse oximetry device to obtain a photoplethysmograph from the throat or oral cavity by the transmission of optical radiation into a tissue site (tissue at the wall of the throat 154, adjacent or at the same level as the carotid arteries), and the detection of the intensity of the optical radiation after absorption by pulsatile blood flow within the tissue site. All three signals (waveforms representative of blood flow, electrocardiogram signal, photoplethysmograph) are utilized to calculate the stroke volume, heart rate, and $SpO_2$ (peripheral capillary oxygen saturation) and to obtain waveforms representative of the arterial flow of central vessels which in this example are one or more of the carotid arteries, but may alternatively be other blood vessels. Cardiac output (CO) is calculated by multiplying stroke volume (SV) by heart rate (HR). When coupled with the values provided by an external blood pressure cuff, real time estimates of arterial blood pressure can also be obtained. Stroke volume variation (SVV) may be determined using methods described in co-pending U.S. patent application Ser. No. 15/433,935 to Lowery, filed on Feb. 15, 2017, and entitled "SYSTEMS AND METHODS FOR OBTAINING CARDIOVASCULAR PARAMETERS," the disclosure of which is hereby incorporated by reference in its entirety for all purposes.

Figure 20:
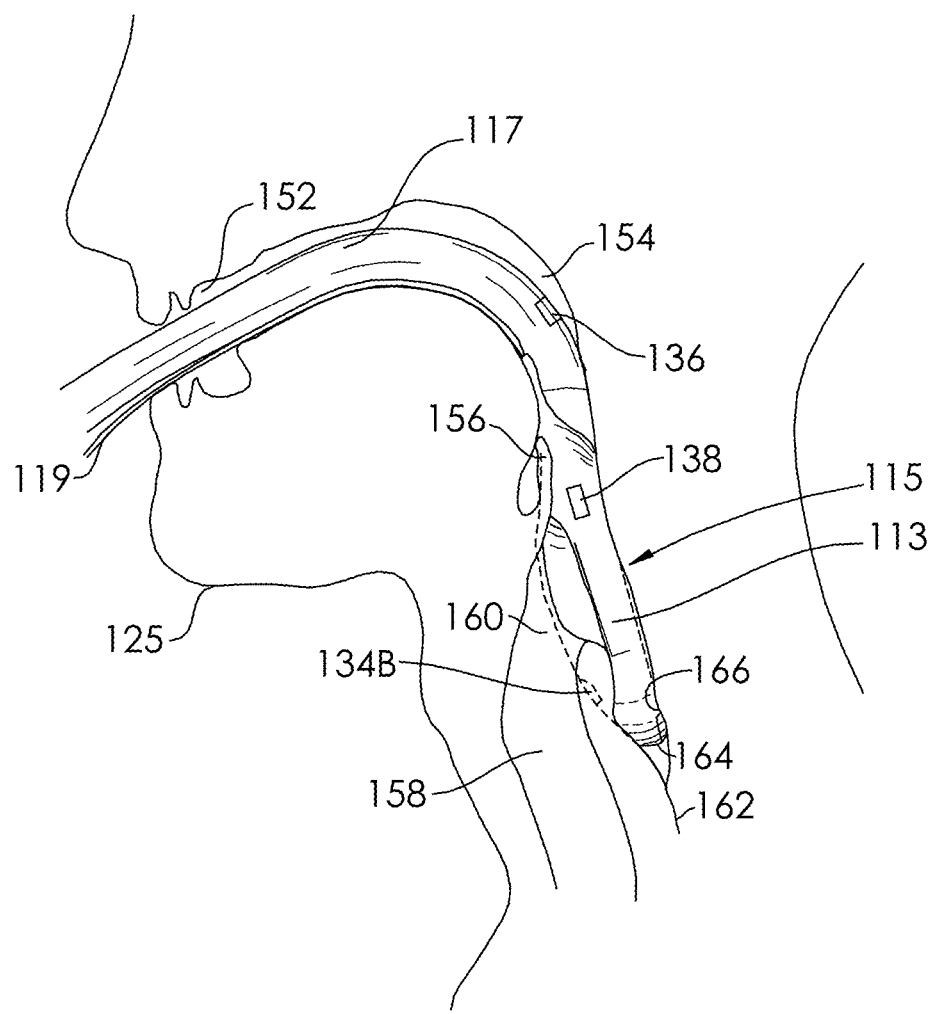
FIG. 20 is a partial sectional view of the laryngeal mask of FIG. 19 in place within a subject.

Turning to FIG. 20, in use, an anesthesiologist or other medical professional positions the LMA 115 so that it covers the larynx 158 of a patient 125. A number of insertion and placement methods may be used. The LMA 115 is shown in FIG. 20 inserted through the mouth 152 of the patient 125 and in place within the throat 154 of the patient 125. The distal end 164 of the LMA 115 is shown adjacent the base 166 of the throat 154, with the cuff 113 shown in relation to the epiglottis 156 and the larynx 158, including the inlet 160 of the larynx. The esophagus 162 is also shown for reference purposes.

Figure 21:
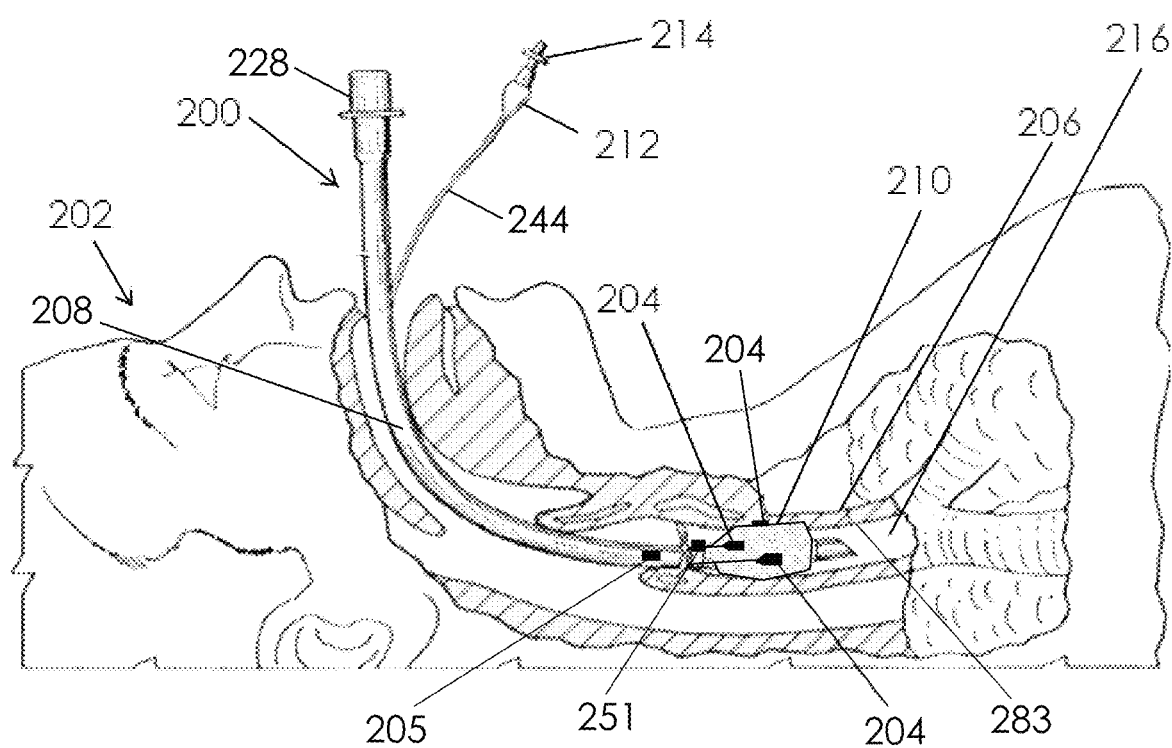
FIG. 21 is a partial sectional view of a system for cardiovascular sensing, according to another embodiment of the present disclosure.
Figure 22:
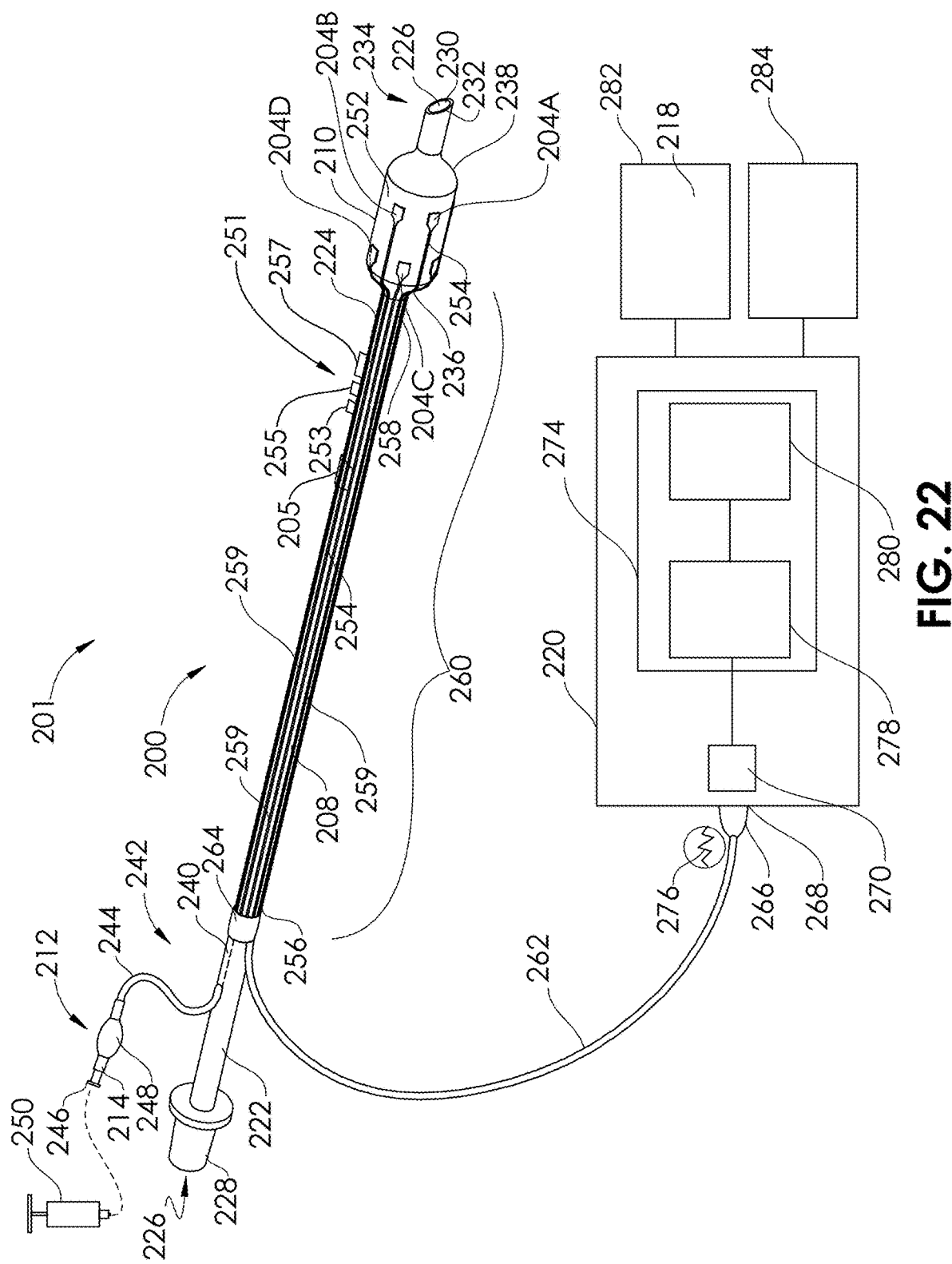
FIG. 22 is perspective view a system for cardiovascular sensing including a sensing device having an expandable member, according to an embodiment of the present disclosure.

In another embodiment, illustrated in FIG. 21, a sensing device 200 is configured for placement in the lumen 216 of a trachea 206 within a patient 202. The sensing device 200 has the functionality of a trachea tube and includes an elongate member 208 and an actuation portion 210 configured to be expanded within the trachea 206. The sensing device 200 is part of a system for measuring cardiovascular parameters 201, which is shown in more detail in FIG. 22. The system for measuring cardiovascular parameters 201 includes a console 220 to which the sensing device 200 may be coupled. The system for measurement of cardiovascular parameters 201 is configured to sense signals related to cardiovascular parameters of the heart. The elongate member 208 of the sensing device 200 may comprise a shaft or catheter tubing. The elongate member 208 has a proximal end 222 and a distal end 224. The sensing device 200 as depicted in FIG. 22 is configured to serve as an endotracheal tube, and thus the sensing device 200 comprises a respiratory lumen 226 extending between a fitting 228, coupled to the proximal end 222 of the elongate member 208 and a port 230 adjacent the distal end 224 of the elongate member 208. The respiratory lumen 226 may be configured to allow the passage of a guidewire (not shown), which may be placed through the respiratory lumen 226 to aid in the delivery of the sensing device 200 within the body cavities of the subject, and which may be subsequently removed. At the port 230, the elongate member 208 may include a skive 232, or angled cut or formed tip, to aid in the tracking of the distal end 234 of the sensing device 200. The fitting 228 is configured to couple to a respiratory or other oxygen or air delivery apparatus, for delivering oxygen and other gases, which may in some cases include an anesthetic, through the respiratory lumen 226 and out the port 230 and into the patient's lungs, for example via the trachea and/or bronchi.

An actuation portion 210 having a proximal end 236 and a distal end 238 is carried by the distal end 224 of the elongate member 208, or may be actually formed from the distal end 224 of the elongate member 208. The actuation portion 210 may comprise an inflatable member, such as a balloon or cuff, or an otherwise expandable structure, and can be configured to have a low-profile state for placement into a body lumen or cavity and delivery within the body lumen or cavity (or within the lumen of a sheath or tube, including a catheter tube). The inflatable member and the elongate member 208 may comprise a polymer such as polyvinyl chloride (PVC) or polyethylene. The actuation portion 210 can also have an expanded state. If the actuation portion 210 is an inflatable member, then the expanded state may be achieved by inflating the actuation portion 210 (inflatable member) with a fluid, such as a gas or liquid. The fluid may include, for example, water, normal saline, air, nitrogen, or other inflation media. An inflation lumen 240 extends from a proximal location 242 to the actuation portion 210 (inflatable member) and is accessed at an interface 212, which may be coupled to the inflation lumen 240 via extension tubing 244. The interface 212 may comprise a luer fitting 246 configured to attach to a syringe or other type of inflation device 250. The interface 212 may include a valve 214, such as a luer-activated valve. The luer-activated valve may be configured to be in a closed (sealed) state when no inflation device is attached to the luer fitting 246, and may be configured to be in an open (unsealed) state when an inflation device is attached to the luer fitting 246. A pilot balloon 248 may be carried on the interface 212 to give tactile or visual feedback for a user to determine the extent of inflation of the inflatable member.

In FIG. 22, the actuation portion 210 is an inflatable member which carries one of more sensors 204 (204A, 204B, 204C, 204D) on its surface 252. Additionally, one or more shaft-based sensors 205 are carried on the elongate member 208. The total number of sensors 204 carried on the actuation portion and sensors 205 carried on the elongate member 208 may be varied in different embodiments. The one or more sensors 204 are secured to the surface 252 of the actuation portion 210 by adhesive or epoxy, or the one of more sensors 204 may be deposited, painted, coated, sprayed, sputtered, or otherwise attached or adhered to the surface 252, as described herein. In some embodiments, the one or more sensors 204 may be applied to the surface 252 of the actuation portion 210 by use of a masking process described herein. In other embodiments, the one or more sensors 204 may be applied by a computer-controlled or robotic applicator which applies the sensor 204 in a computer-controlled pattern to the surface 252. In some embodiments, the one or more sensors 204, 205 are electrodes comprising an electrically conductive material, which may comprise silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 204, 205 under radiography or fluoroscopy. Returning to FIG. 21, the valve 214 maintains the desired inflated pressure, and thus maintains the contact of the sensors 204 with the interior wall 283 of the trachea 206.

One or more optical sensors 251, each comprising at least two light emitting sources 253, 255 and one light detector 257, are carried on the elongate member 208. As in the system for measurement of cardiovascular parameters 100 of FIG. 19, the optical sensor 251 is configured to obtain plethysmographic data when it is positioned in spaced relation with tissue, for example, in a non-contact arrangement with an inner wall of a body lumen. Also, as in the system for measurement of cardiovascular parameters 100 of FIG. 19, the sensors 204 utilize bio-impedance to generate waveforms representative of the pulsatile flow of blood. However, because the actuation portion 210 is configured to be placed in the trachea, the adjacent area having significant pulsatile blood flow is the ascending aorta or central vasculature. The ascending aorta represents blood flow close to that of the cardiac output; Doppler methods often rely on the descending aorta for measurements of stroke volume, which does not include flow from the head and upper body portions.

Though the actuation portion 210 is configured to be expanded within the trachea 206, in alternative embodiments, the sensing device 200 may be placed inside the esophagus of a subject, and the actuation portion 210 expanded such that the sensors 204 contact an interior wall of the esophagus. In keeping with the teachings of this disclosure, one or more electrically-conductive tracings 259, each having a proximal end 256 and a distal end 258, are carried upon internally-facing surfaces and/or externally-facing surfaces of the elongate member 208. Electrically-conductive tracings 254 carried on the surface 252 of the actuation portion 210 connect the sensors 204A-D with the electrically-conductive tracings 259. One or more electrically-conductive tracings 259 connect the one or more optical sensors 251 and the one or more sensors 204, 205 (with or without the use of intermediate electrically-conductive tracings 254) to a cable 262, which terminates in a connector 266 which is configured to be coupled to an input 268 of a console 220. A dielectric layer 260 is subsequently applied, where necessary, over the one or more electrically-conductive tracings 259 or electrically-conductive tracings 254

Signals 276 entering the console 220 may in some embodiments represent several different sensors 204, 205, 251 (having been carried by several corresponding electrically-conductive tracings 259, 254). In some embodiments, the console 220 may include an analog-to-digital converter 270 through which the one or more signals 276 are converted. In some embodiments, the signals 276 may be multiplexed. The one or more signals 276 may enter a processor 274 provided by the console 220. The processor 274 may include one or more amplifiers 278 for amplifying the signal 276 and one or more filters 280 for filtering the signal 276. A display 282 is configured to display a resulting graphic representation 218. The graphic representation 218 may simply be a parameter value or a table of values, or may actually be a graph of data. The display 282 may be built in to the console 220 or may be separate. The display 282 may be directly connected to the console 220 or may be remote and communicate wirelessly. The console 220 may include an interface 284 which allows a user to control and/or communicate with the console 220 or the system for measurement of cardiovascular parameters in general. The interface 284 may even allow a user to control or communicate with the sensing device 200, for example, if the sensing device 200 incorporates an internal microprocessor, which may be carried on a flex circuit. The interface 284 may be a touch screen, a keyboard, an audio communication system (e.g., voice-activated), and may incorporate a graphic user interface (GUI).

Figure 23:
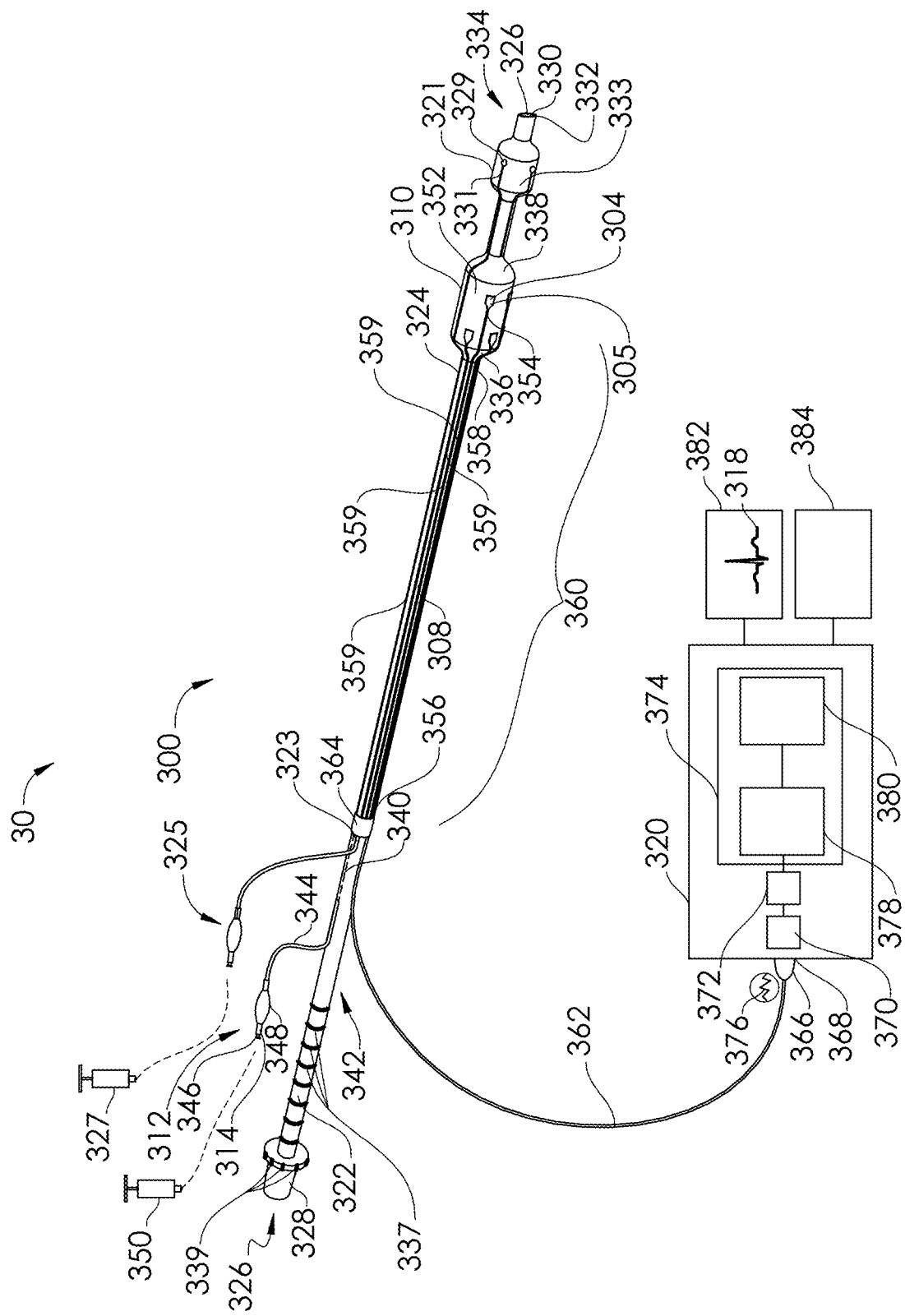
FIG. 23 is a perspective view of a system for sensing electrical activity of the heart according to an embodiment of the present disclosure.

FIG. 23 illustrates a sensing system 30 comprising a sensing device 300 which is configured to be coupled to a console 320. The sensing system 30 is configured to sense signals from the interior of a subject. Such signals may result from bio-impedance, as previously described. Additionally, or alternatively, the signals may include signals related to electrical activity of the heart, such as can be acquired to provide an electrocardiogram. The sensing device 300 comprises an elongate member 308, which may comprise a shaft or catheter tubing. The elongate member 308 has a proximal end 322 and a distal end 324. The sensing device 300 as depicted in FIG. 23 is configured to serve as an endotracheal tube having sub-selective capability, and thus the sensing device 300 comprises a respiratory lumen 326 extending between a fitting 328, coupled to the proximal end 322 of the elongate member 308 and a port 330 adjacent the distal end 324 of the elongate member 308. The respiratory lumen 326 may be configured to allow the passage of a guidewire (not shown), which may be placed through the respiratory lumen 326 to aid in the delivery of the sensing device 300 within the body cavities of the subject, and which may be subsequently removed. At the port 330, the elongate member 308 may include a skive 332, or angled cut or form, to aid in the tracking of the distal end 334 of the sensing device 300. The fitting 328 is configured to couple to a respiratory or other oxygen or air delivery apparatus, for delivering oxygen and other gases, which may in some cases include an anesthetic, through the respiratory lumen 326 and out the port 330 in into the patient's lungs, for example via one or more bronchi.

A first actuation portion 310 having a proximal end 336 and a distal end 338 is carried by the distal end 324 of the elongate member 308, or may be actually formed from the distal end 324 of the elongate member 308. The first actuation portion 310 may comprise an inflatable member, such as a balloon or cuff, or an otherwise expandable structure, and can be configured to have a low-profile state for placement into a body lumen or cavity and delivery within the body lumen or cavity (or within the lumen of a sheath or tube, including a catheter tube). The first actuation portion 310 can also have an expanded state. If the first actuation portion 310 is an inflatable member, then the expanded state may be achieved by inflating the first actuation portion 310 (inflatable member) with a fluid, such as a gas or liquid. The fluid may include, for example, water, normal saline, air, nitrogen, or other inflation media. An inflation lumen 340 extends from a proximal location 342 to the first actuation portion 310 (inflatable member) and is accessed at an interface 312, which may be coupled to the inflation lumen 340 via extension tubing 344. The interface 312 may comprises a luer fitting 346 configured to attach to a syringe or other type of inflation device 350. The interface 312 may include a valve 314, such as a luer-activated valve. The luer-activated valve may be configured to be in a closed (sealed) state when no inflation device is attached to the luer fitting 346, and may be configured to be in an open (unsealed) state when an inflation device is attached to the luer fitting 346. A pilot balloon 348 may be carried on the interface 312 to give tactile or visual feedback for a user to determine the extent of inflation of the inflatable member. Distal to the first actuation portion 310 is a second actuation portion 321 which is expandable. The second actuation portion 321 may be an inflatable member, such as a balloon or cuff, and may be expandable through the same inflation lumen 340 as the first actuation member 310, or, as illustrated, may be independently expandable through a second inflation lumen 323 via a second interface 325, which may have similar features to the interface 312. For example, the second interface 325 may be inflated by an inflation device 327. In some embodiments, the first actuation member 310 may be configured to be inflated within a trachea 206 (FIG. 24) while the second actuation portion 321 may be configured to be inflated within a bronchus 215, 217. In some embodiments, the first actuation portion 310 has a larger profile or diameter than the second actuation portion 321. For example, the diameter of the first actuation portion 310 may be between about 5 mm and about 30 mm, or between about 13 mm and about 27 mm, while the diameter of the second actuation portion 321 may be between about 4 mm and 20 mm, or between about 9 mm and about 18 mm.

In FIG. 23, the first actuation portion 310 is an inflatable member which carries one of more sensors 304 on its surface 352. The one or more sensors 304 may be secured to the surface 352 of the first actuation portion 310 by adhesive or epoxy, or the one of more sensors 304 may be deposited, painted, coated, sprayed, sputtered, or otherwise attached or adhered to the surface 352, as described herein. In some embodiments, the one or more sensors 304 may be applied to the surface 352 of the first actuation portion 310 by use of a masking process described herein. In other embodiments, the one or more sensors 304 may be applied by a computer-controlled or robotic applicator which applies the sensor 304 in a computer-controlled pattern to the surface 352. In some embodiments, the one or more sensors 304 are electrodes comprising an electrically conductive material, which may comprise silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 304 under radiography or fluoroscopy.

The one or more sensors each have a contact surface 305. Each of the one or more sensors 304 may be coupled to a conductor 354. One or more electrically-conductive tracings 359 are applied to internally-facing surfaces and/or externally-facing surfaces of the elongate member 308, each of the one or more electrically-conductive tracings 359 having a proximal end 356 and a distal end 358. In some embodiments, the one or more sensors 304 and/or the one or more conductors 354, 359 may be applied using methods described in U.S. Pat. No. 9,289,141 entitled "Apparatus and Methods for the Measurement of Cardiac Output," issued Mar. 22, 2016. The one or more conductors 354 or one or more electrically-conductive tracings 359 may be applied at the same time as the one or more sensors 304 or may be applied before or after the application of the one or more sensors 304. In some embodiments, the one or more sensors 304 are partially applied (e.g., a single layer or a first number of layers), the one or more conductors 354 or one or more electrically-conductive tracings 359 are then applied, and then a final one or more layers are applied to complete the one or more sensors 304. In some embodiments, a dielectric layer 360 is subsequently applied over the one or more electrically-conductive tracings 359 after their application. One or more sensors 329 and one or more conductors 331 are applied to a surface 333 of the second actuation portion 321 by any of the methods described. The one or more conductors 354, 331 may also be coated or otherwise covered by a dielectric material. The one or more electrically-conductive tracings 359 couple the sensors 304, 329 and/or the conductors 331, 354 to a cable 362 (for example, with solder), and a covering or strain relief 364 may be secured over the area of connection. The covering or strain relief 364 may be a dielectric material, including polyimide, adhesive or epoxy, polyethylene or polyester shrink tubing or other similar materials or combinations thereof.

The cable 362 includes a connector 366 which is configured to be coupled to an input 368 of the console 320 and is configured to carry signals 376 from the one or more sensors 304 and/or one or more sensors 329 to the console 320. Signals 376 entering the console 320 may in some embodiments represent several different sensors 304, 329 (having been carried by several corresponding conductors 354, 331 and electrically-conductive tracings 359). In some embodiments, the console 320 may include a lead selector 370 to allow selection of a signal 376 from a particular one of the one or more sensors 304, 329. In some embodiments, one or more signals 376 from one or more sensors 304, 329 may be processed in parallel. The console 320 may include a protection circuit 372, which may include a circuit breaker or other circuit protection device. The one or more signals 376 may enter a processor 374 provided by the console 320. The processor 374 in some embodiments includes one or more amplifiers 378 for amplifying the signal 376 and one or more filters 380 for filtering the signal 376. A display 382 is configured to display a resulting electrocardiogram signal 318 or trace (e.g., PQRST waveform) from the console 320. The display 382 may be built in to the console 320 or may be separate. The display 382 may be directly connect to the console 320 or may be remote and communicate wirelessly. The console 320 may include an interface 384 which allows a user to control and/or communicate with the console 320 or the sensing system 30 in general. The interface may even allow a user to control or communicate with the sensing device 300, for example, if the sensing device 300 incorporates an internal microprocessor, which may be carried on a flex circuit. The interface 384 may be a touch screen, a keyboard, an audio communication system (e.g., voice-activated), and may incorporate a graphic user interface (GUI).

Depth markings 337 and rotational reference markings 339 allow a user to determine the orientation of the sensing device 300 by sight, at the proximal end of the sensing device 300. In some embodiments, an additional sensor may be carried on the second actuation portion 321 which is configured to measure venous oxygenation. The additional sensor may comprise an optical oxygen saturation sensor.

Figure 24:
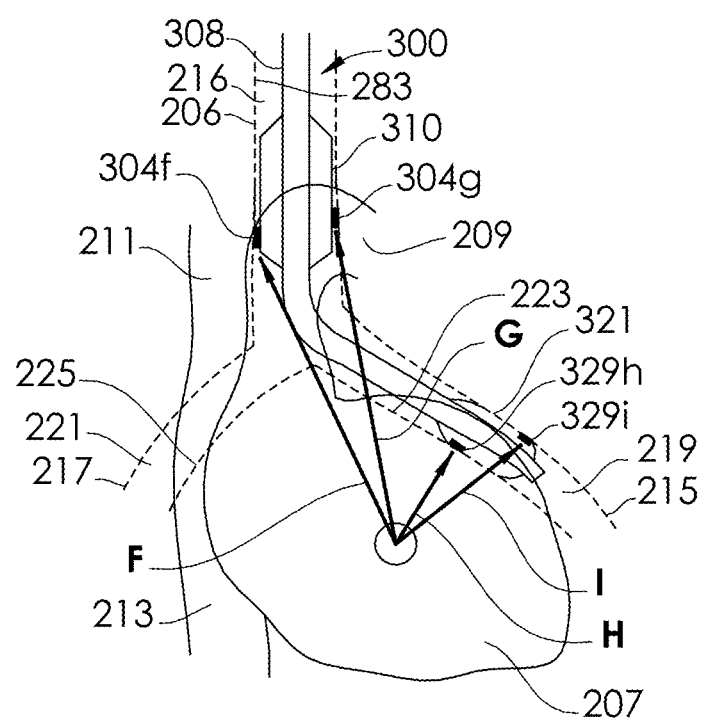
FIG. 24 is a view of a sensing device placed within the trachea and a bronchus of a subject according to an embodiment of the present disclosure.

A sensing device 300 is shown in FIG. 24 having sensors 304f, 304g disposed on its first actuation portion 310 which has been located and expanded within the lumen 216 of the trachea 206. In addition, sensors 329h, 329i are disposed on the second actuation portion 321 of the sensing device 300, and the second actuation portion 321 has been located and expanded within a lumen 219 of left bronchus 215. Each of the sensors 304f, 304g are contacting the interior wall 283 of the trachea 206, thus being electrodes for a lead F and lead G, respectively. A first vector F indicates lead F and vector G indicates lead G. Each of the sensors 329h, 329i are contacting an interior wall 223 of the left bronchus 215, thus being electrodes for a lead H and lead I, respectively. Vector H indicates lead H and vector I indicates lead I. Alternatively, the second actuation portion 321 of the sensing device 300 may be tracked into the lumen 221 of right bronchus 217 so that sensors 329 carried on the second actuation portion 321 are able to contact an interior wall 225 of the right bronchus 217. In order to obtain differently-oriented vectors. For orientational reference purposes, the heart 207, the aorta 209, the superior vena cava 211, and the inferior vena cava 213 of the patient are illustrated. Methods and apparatus for acquiring ECG signals are described in International Application (PCT) Publication No. WO 2016/179563 to Lowery, entitled "SYSTEMS AND METHODS FOR INTERNAL ECG ACQUISITION," published Nov. 10, 2016.

Figure 25:
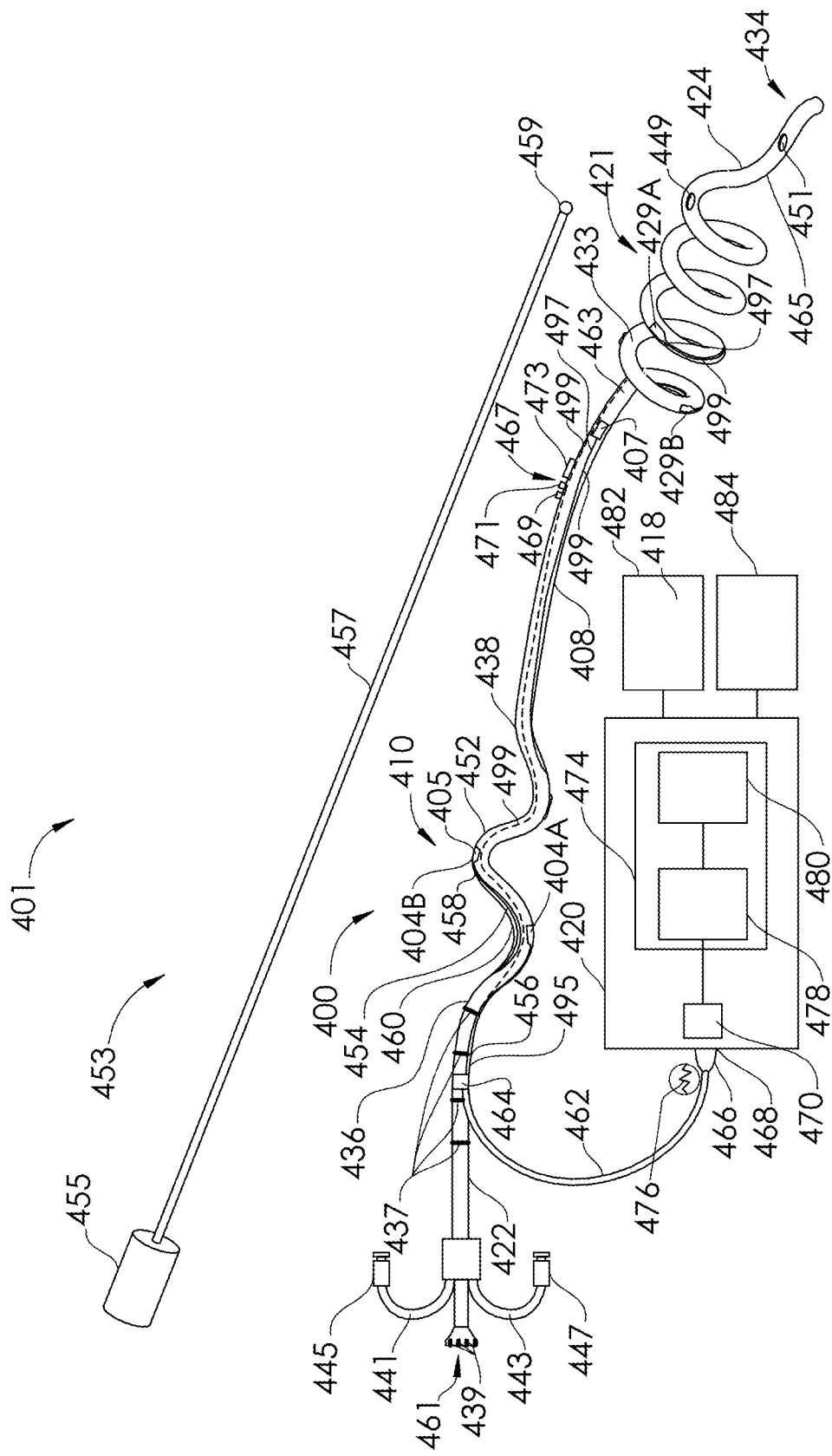
FIG. 25 is perspective view a system for cardiovascular sensing including a sensing device, according to an embodiment of the present disclosure.

FIG. 25 illustrates a system for measurement of cardiovascular parameters 401 comprising a sensing device 400 which is configured to be coupled to a console 420. The sensing system 401 is configured to sense signals related to cardiovascular parameters of the heart, but may be alternatively configured for internally obtaining ECG information. The sensing device 400 comprises an elongate member 408, which may comprise a shaft or catheter tubing. The elongate member 408 has a proximal end 422 and a distal end 424. The sensing device 400 as depicted in FIG. 25 is configured to serve as a nasogastric tube (NG tube), and thus the sensing device 400 comprises one or more lumens 441, 443 extending between one or more fittings 445, 447 coupled to the proximal end 422 of the elongate member 408 and extending through the elongate member until terminating at one or more ports 449, 451 adjacent the distal end 424 of the elongate member 408. One of the ports 449, 451 may be configured for delivery of one or more medicants or for delivery of other fluids (e.g., normal saline) or for delivery of enteral feeding solutions. The ports 449, 451 may be located for direct delivery of the fluids into the stomach, but in alternative embodiments, the sensing device may be configured to allow at least one of the ports 449, 451 to be located in the duodenum or jejunum for direct delivery. In some cases, the port 449, 451 may be located in the distal esophagus. In some embodiments, one of the lumens 441, 443 may be dedicated to fluid delivery while the other lumen 441, 443 is dedicated to suction or lavage of internal contents, for example, stomach contents. In some embodiments, both of the lumens 441, 443 are capable of both delivery and suction or lavage. In some embodiments, the fittings 445, 447 comprises luer fittings, configured to couple to luer fittings of various delivery or suction devices.

Figure 26:
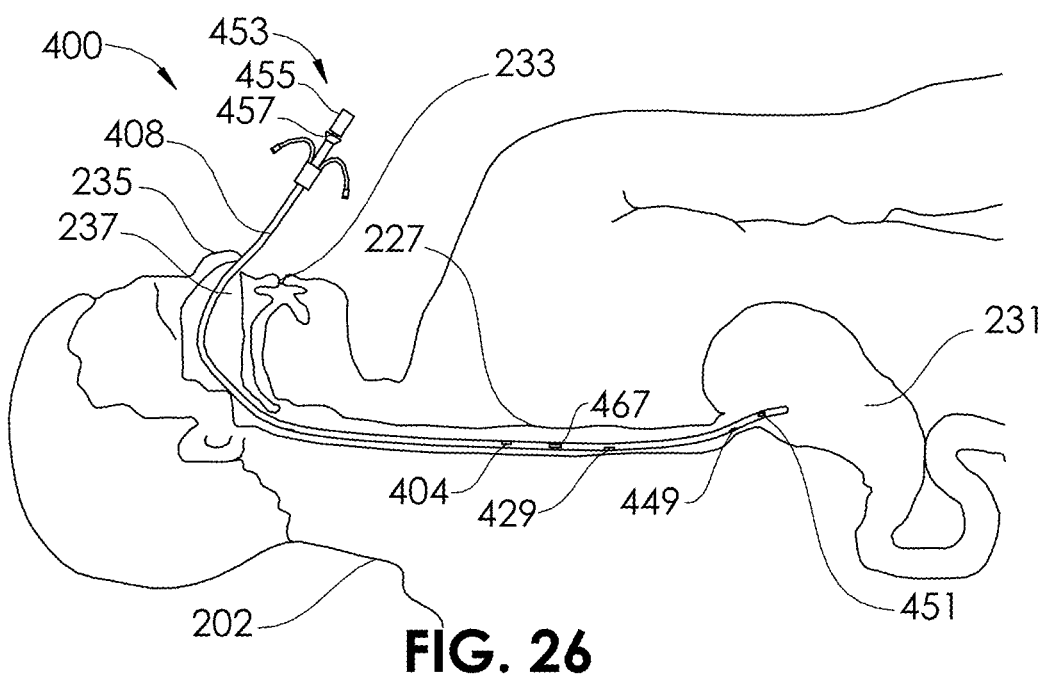
FIG. 26 is a partial sectional view of the sensing device of FIG. 25 within an esophagus of a subject in a low-profile state, according to an embodiment of the present disclosure.
Figure 27:
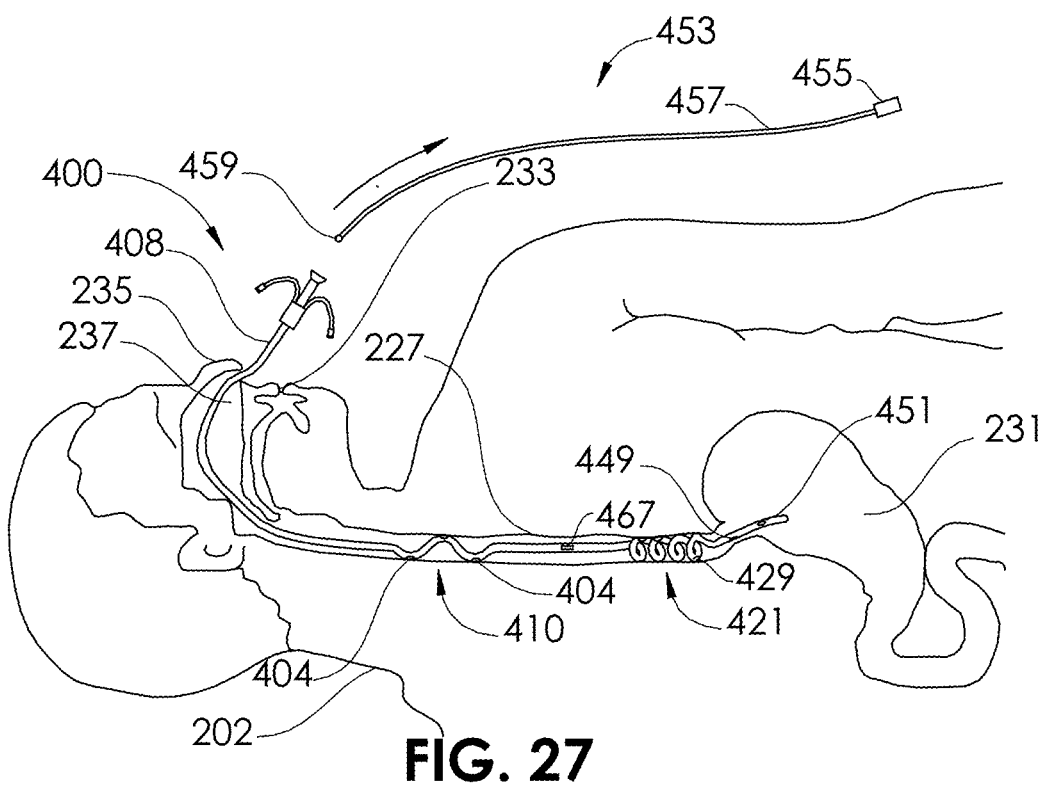
FIG. 27 is a partial sectional view of the sensing device of FIG. 25 within an esophagus of a subject in an expanded state, according to an embodiment of the present disclosure.

A first actuation portion 410 having a proximal end 436 and a distal end 438 is carried by the elongate member 408. As illustrated in FIG. 25, the first actuation portion 410 in this particular embodiment comprises a secondary shape having an enlarged profile (in comparison to the diameter of the elongate member 408 shaft). The secondary shape is illustrated in FIG. 25 as a serpentine shape or S-shape formed directly in the elongate member 408. The shape may be formed by heat forming of a thermoplastic tubing. A stylet 453 having a proximal hub 455 and an elongate body 457 having a rounded or otherwise blunt tip 459 is configured to be placed down a central lumen 461 of the elongate member 408 of the sensing device 400. FIG. 26 illustrates the sensing device 400 in use, with the elongate body 457 of the stylet 453 inserted within the central lumen 461, causing the first actuation portion 410 to assume a linear or substantially linear orientation, to aid in delivery or movement within a body cavity or lumen. When the sensing device 400 has been delivered to a desired location in the body lumen, for example, the esophagus and stomach, the elongate body 457 of the stylet 453 may be retracted or completely removed from the central lumen 461 of the sensing device 400, to allow the first actuation portion 410 to assume its secondary shape having an enlarged profile (FIG. 27). In other embodiments, the elongate member 408 may comprise a shape memory polymer having shape memory which allows the first actuation portion 410 to achieve its desired secondary shape by contact with a patient's body temperature, or by introduction of a fluid having an increased temperature (e.g., 42° C.) around the elongate member 408. In another alternative embodiment, a shaped shape-memory alloy (e.g., Nitinol) resides within the elongate member 408 and causes the elongate member 408 to change shape at the first actuation portion 410 and/or the second actuation portion 421 when exposed to an elevated temperature (e.g., body temperature or an increased temperature, such as a temperature up to 42° C.). Alternatively, the first actuation portion 410 may be replaced by an inflatable member, such as a balloon or cuff such as those described in prior embodiments herein. In general, the first actuation portion 410 comprises an expandable structure, and can be configured to have a low-profile state for placement into a body lumen or cavity and delivery within the body lumen or cavity (or within the lumen of a sheath or tube, including a catheter tube). As described, the first actuation portion 410 can also have an expanded state.

Distal to the first actuation portion 410 is a second actuation portion 421 having a proximal end 463 and a distal end 465. The second actuation portion 421 is expandable and comprises a low-profile state (FIG. 26) which may be achieved by placement of the elongate body 457 of the stylet 453 through the central lumen 461, and an expanded state (FIGS. 25 and 27) which may be achieved by removal or retraction of the elongate body 457 of the stylet 453 from the central lumen 461. The secondary shape is illustrated in FIGS. 25 and 27 as a spiral or helical shape formed directly in the elongate member 408. Any of the forming materials or methods used in relation to the first actuation portion 410 may also be used in relation to the second actuation portion 421. In some embodiments, the first actuation member 410 may be configured to be expanded within the esophagus while the second actuation portion 421 may be configured to be expanded within the esophagus at a location distal to the first actuation member 410. In some embodiments, the first actuation portion 410 has a smaller profile or diameter than the second actuation portion 421. For example, the (expanded) diameter of the first actuation portion 410 may be between about 15 mm and about 30 mm, or between about 20 mm and about 27 mm, while the (expanded) diameter of the second actuation portion 421 may be between about 25 mm and 40 mm, or between about 30 mm and about 37 mm. In some embodiments, both of the actuation portions 410, 421 may be spiral or helical. In some embodiments, both of the actuation portions 410, 421 may be serpentine or S-shaped. In some embodiments, the first actuation portion 410 may be spiral or helical and the second actuation portion 421 may be serpentine or S-shaped. Other three-dimensional or two-dimensional shapes may be used. In some embodiments, there may only be a single actuation portion, or in other embodiments, there may be three of more actuation portions. Though the ports 449, 451 are shown adjacent a distal end 434 of the sensing device 400, one or more ports 449, 451 may be located some distance proximal to the distal end 434, and in some embodiments proximal to the second actuation portion 421, and in some embodiments, even proximal to the first actuation portion 410. Markings 437, 439 can be utilized in the sensing device 400 as described in relation to the sensing device 300 of FIG. 23.

In FIG. 25, the first actuation portion 410 carries one of more sensors 404 (404A, 404B) on its outwardly-extending surfaces 452 (e.g., near the outer apex of a curve), such that the one or more sensors 404 are directed against an interior wall of the esophagus (or other body lumen) when the first actuation portion 410 is in its expanded state. Additionally, one or more shaft-based sensors 407 are carried on the elongate member 408. The total number of sensors 404 carried on the actuation portion and sensors 407 carried on the elongate member 408 may be varied in different embodiments. The one or more sensors 404 may be secured to the surface 452 of the first actuation portion 410 by adhesive or epoxy, or the one of more sensors 404 may be deposited, painted, coated, sprayed, sputtered, or otherwise attached or adhered to the surface 452, as described herein. In some embodiments, the one or more sensors 404 may be applied to the surface 452 of the first actuation portion 410 by use of a masking process described herein. In other embodiments, the one or more sensors 404 may be applied by a computer-controlled or robotic applicator which applies the sensor 404 in a computer-controlled pattern to the surface 452. In some embodiments, the one or more sensors 404, 407 are electrodes comprising an electrically conductive material, which may comprise silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 404, 407 under radiography or fluoroscopy.

One or more optical sensors 467, each comprising at least two light emitting sources 469, 471 and one light detector 473, are carried on the elongate member 408. The optical sensor 467 is configured to obtain plethysmographic data when it is positioned in spaced relation with tissue, for example, in a non-contact arrangement with an inner wall of a body lumen. Also, the sensors 404, 429 utilize bio-impedance to generate waveforms representative of the pulsatile flow of blood. Because the actuation portion 410 is configured to be placed in the esophagus, the adjacent area having significant pulsatile blood flow is the ascending aorta.

The sensors 404, 407, 429 are also used to obtain an electrocardiogram signal from the body of the patient to provide electrical timing information, as described in international publication number WO2016/179563, published on Nov. 10, 2016, and entitled "SYSTEMS AND METHODS FOR INTERNAL ECG ACQUISITION."

The one or more sensors 404 each have a contact surface 405. Each of the one or more sensors 404, 429 or the one or more optical sensors 467 may be coupled to an electrically-conductive tracing 454 having a proximal end 456 and a distal end 458 or electrically-conductive tracing 499 having a proximal end 495 and a distal end 497. One or more electrically-conductive tracings 454, 499 are carried on externally-facing surfaces and/or internally-facing surfaces on or within the elongate member 408. The one or more electrically-conductive tracings 454, 499 may be applied at the same time as the one or more sensors 404, 429 or may be applied before or after the application of the one or more sensors 404. In some embodiments, the one or more sensors 404, 429 are partially applied (e.g., a single layer or a first number of layers), the one or more electrically-conductive tracings 454, 499 are then applied, and then a final one or more layers are applied to complete the one or more sensors 404, 429. In some embodiments, a dielectric layer 460 is subsequently applied over the one or more electrically-conductive tracings 454, 499, as required, after the application of the one or more electrically-conductive tracings 454, 499. One or more sensors 429 (429A, 429B) are applied to outwardly-extending surfaces 433 of the second actuation portion 421 by any of the methods described. Thus, the electrically-conductive tracings 454, 499 are configured to carry signals from the one or more sensors 404, 429, 407 and one or more optical sensors 467 to individual conductors in a cable 462. The cable 462 is electrically coupled to the proximal ends 456 of the one or more electrically-conductive tracings 454, 499 (for example, with solder), and a covering or strain relief 464 may be secured over the area of connection. The covering or strain relief 464 may be a dielectric material, including polyimide, adhesive or epoxy, polyethylene or polyester shrink tubing or other similar materials or combinations thereof.

The cable 462 includes a connector 466 which is configured to be coupled to an input 468 of the console 420 and is configured to carry signals 476 from the one or more sensors 404, one or more sensors 429, and the one or more optical sensors 467 to the console 420. Signals 476 entering the console 420 may in some embodiments represent several different sensors 404, 429 (having been carried by several corresponding electrically-conductive tracings 454, 499). In some embodiments, the console 420 may include an analog-to-digital converter 470 through which the one or more signals 476 are converted. In some embodiments, the signals 476 may be multiplexed. The one or more signals 476 may enter a processor 474 provided by the console 420. The processor 474 in some embodiments includes one or more amplifiers 478 for amplifying the signal 476 and one or more filters 480 for filtering the signal 476. A display 482 is configured to display a resulting graphic representation 418. The graphic representation 418 may simply be a parameter value or a table of values, or may actually be a graph of data. The display 482 may be built in to the console 420 or may be separate. The display 482 may be directly connected to the console 420 or may be remote and communicate wirelessly. The console 420 may include an interface 484 which allows a user to control and/or communicate with the console 420 or the system for measurement of cardiovascular parameters in general. The interface may even allow a user to control or communicate with the sensing device 400, for example, if the sensing device 400 incorporates an internal microprocessor, which may be carried on a flex circuit. The interface 484 may be a touch screen, a keyboard, an audio communication system (e.g., voice-activated), and may incorporate a graphic user interface (GUI).

The system for measurement of cardiovascular parameters 401 described herein is useful to measure physiological functions/parameters in mammalian subjects, including stroke volume, cardiac output, and stroke volume variation. Once the actuation portion 410, 421 is positioned and expanded, a current is injected into the subject's tissue through one of the electrodes (sensors 404, 429, 407) serving as a current electrode, a voltage is established between the current electrode and the ground electrode (one of sensors 404, 429, 407) so that a current flows through the tissue disposed between the current electrode and the ground electrode. With one or more sense electrodes (sensors 404, 429), the voltages caused by the current flowing in the tissue are detected, wherein the voltages vary in accordance with changes in the bioelectrical impedance of the tissue.

A sensing device 400 is shown in FIG. 26 with the stylet 453 inserted inside the elongate member 408 and being delivered through the nasal cavity 237 of the nose 235 of a patient 202 and into the esophagus 227. The mouth 233 is shown as a reference point. In FIG. 27, the stylet 453 is removed from the sensing device 400 and the elongate member 408 is adjusted as necessary so that the first actuation portion 410 and second actuation portion 421 assume their secondary expanded states in their desired locations. The sensors 404, 429 are applied against interior wall portions of the esophagus 227 by the first actuation portion 410 and second actuation portion 421. Port 451 has been placed into the interior of the stomach 231 for fluid delivery, suction, lavage, or other procedural purposes.

The optical sensor 467, when the actuation portion 410 is expanded within the esophagus 227, is in a spaced (non-contact) relation with the interior wall of the esophagus, thus allowing for the reflectance of the optical radiation.

In the embodiments presented in FIGS. 19-27, it should be understood that any of the configurations presented in FIGS. 7-12 may be utilized as the tube 117 or elongate member 208, 308, 408, depending on the number of electrically-conductive tracings required and/or the orientation of the electrically-conductive tracings that is most efficient. Additionally, other alternatives of the configurations presented in FIGS. 7-12 are also contemplated which utilize variations of the number of elongate members/tubes or number and orientation of the electrically-conductive tracings. Furthermore, in any of the embodiments presented in FIGS. 19-27, the configurations of the connectors 1054, 1154 of FIGS. 13-18, or variations of these embodiments may be utilized, again, depending on the particular requirements of number of electrically-conductive tracings and their orientation.

Figure 28:
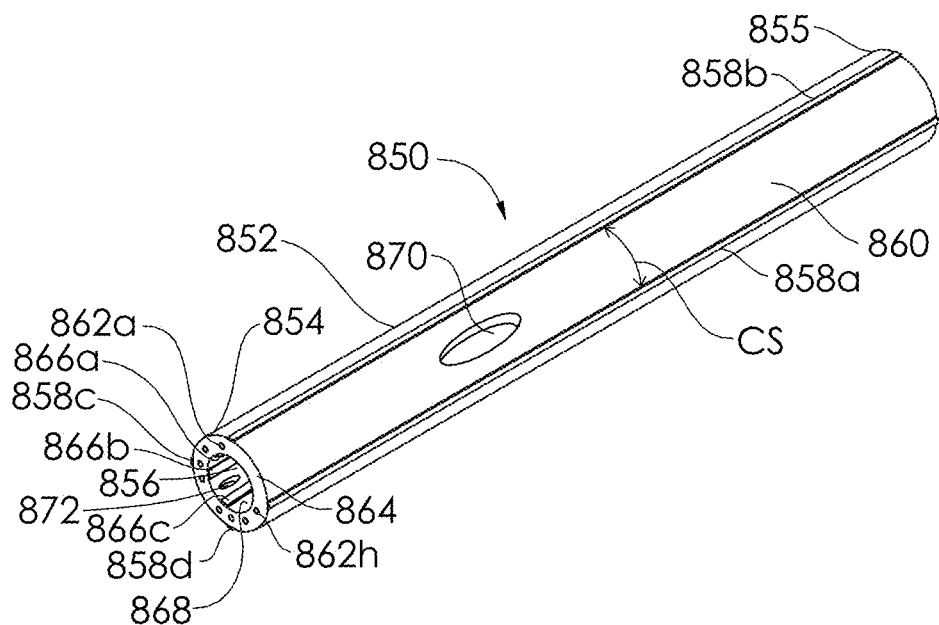
FIG. 28 is a perspective view of a tubular component of a medical device according to an embodiment of the present disclosure.

FIG. 28 illustrates an alternative embodiment of a medical device body 850 comprising an elongate member 852 having a lumen 856 extending therethrough. There are eight elongate conductors 862a-h, which may include copper wire, embedded in the wall 864 of the elongate member 852. The wire may alternately comprise other conductive materials, such as silver, gold, or platinum. In some special cases, the wire may even comprise less conductive materials such as stainless steel. The elongate conductors may have a diameter of between about 0.004 inches and about 0.012 inches, or about 0.005 inches to about 0.010 inches, or about 0.006 inches to about 0.009 inches. The elongate conductors 862 may include a dielectric coating, but this may not be necessary if the material of the elongate member is an electrically insulative polymer, such as polyvinyl chloride (PVC), or other insulative polymers. Electrically-conductive tracings 866a-c are applied onto an inner surface 868 and electrically-conductive tracings 858a-d are applied onto an outer surface 860 by the methods disclosed herein, thus creating a composite multi-conductor (wires and tracings) system. The combination of wires 862 embedded within the wall 864 of the elongate member 852, electrically-conductive tracings 866 on the inner surface 868, and electrically-conductive tracings 858 on the outer surface 860 allows the incorporation of an even larger number of conductors to carry signals from one end 854 to the other end 855 of the elongate member 852.

Additionally, a first orifice 870 and second orifice 872 can be created in the wall 864 of the elongate member 852 (tubing) without damaging any of the elongate conductors 862 or electrically-conductive tracings 858, 866. As shown in FIG. 28, a circumferential space CS exists between electrically-conductive tracing 858a and electrically-conductive tracing 858b. This circumferential space CS is also between conductor 862a and 862h. Furthermore, the circumferential space CS is between electrically-conductive tracing 866a and electrically-conductive tracing 866c. Thus, there are no electrically-conductive tracings 858, 866 or conductors 862 within the circumferential space CS. Thus, a first orifice 870 is made (e.g., by drilling or cutting) in a single wall thickness of the elongate member 852 to fluidly connect the lumen 856 to the external environment. In order to assure that no electrically-conductive tracings 858, 866 or conductors 862 are damaged upon constructing the first orifice 870, the circumferential orientation of the conductors 862 is controlled during the embedding process (e.g., co-extrusion, over-extrusion, multilayer-extrusion). Additionally, the circumferential orientation of each of the electrically-conductive tracings 858, 866 is controlled with respect to the circumferential orientation of the conductors 862.

The second orifice 872 is made in a single wall thickness of the elongate member 852 to fluidly connect the lumen 856 to the external environment. The second orifice 872 is made by drilling or cutting through the wall 864 between electrically-conductive tracing 858c and electrically-conductive tracing 858d, between conductor 862d and 862e, and between electrically-conductive tracing 866b and electrically-conductive tracing 866c. In order to assure that no electrically-conductive tracings 858, 866 or conductors 862 are damaged upon constructing the second orifice 872, the circumferential orientation of the conductors 862 is controlled during the embedding process (e.g., co-extrusion, over-extrusion, multilayer-extrusion), and the circumferential orientation of each of the electrically-conductive tracings 858, 866 is controlled with respect to the circumferential orientation of the conductors 862.

Figure 29:
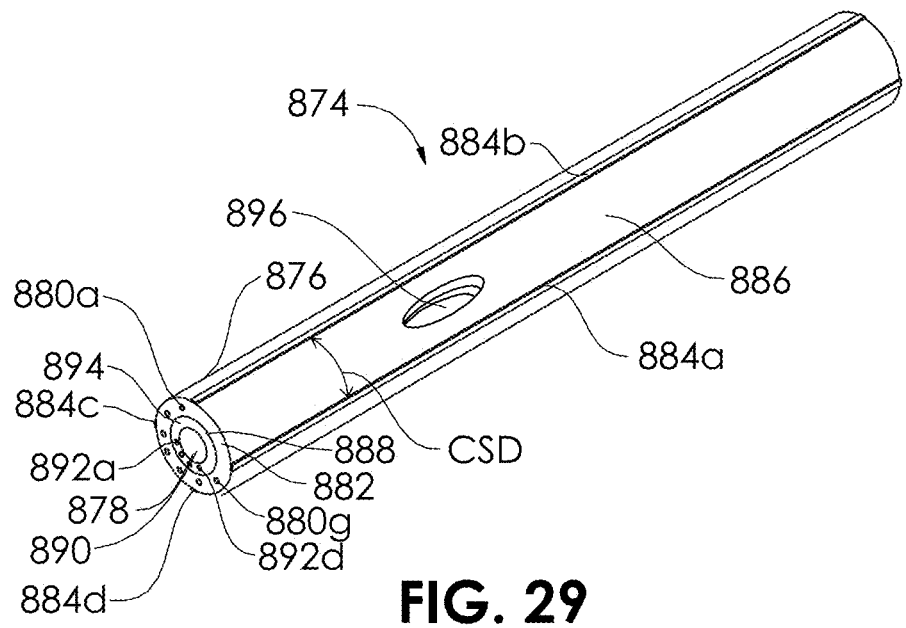
FIG. 29 is a perspective view of a tubular component of a medical device according to an embodiment of the present disclosure.

FIG. 29 illustrates an alternative embodiment of a medical device body 874 that, like the medical device body 850 of FIG. 28, includes a composite conductor structure. The medical device body 874 comprises an elongate member 876 having a lumen 878 extending therethrough. There are seven elongate conductors 880a-g, which may include copper wire, embedded in the wall 882 of the elongate member 876. Electrically-conductive tracings 884a-d are applied onto an outer surface 886 of the elongate member 876. The elongate member 876 is coupled to an elongate member 888 having a lumen 890. The elongate member 888 includes four elongate conductors 892a-d embedded in its wall 894. There is a circumferential space CSD between electrically-conductive tracing 884a and electrically-conductive tracing 884b. This circumferential space CSD includes a portion of the space between conductor 880a and conductor 880g, and a portion of the space between conductor 892a and conductor 892d. Thus, an orifice 896 is safely made through the wall 882 of the elongate member 876 and the wall 894 of the elongate member 888, without causing any damage to the conductors 880, 892 or the electrically-conductive tracings 884. The circumferential orientation of the conductors 880 and the conductors 892 is controlled during each of the embedding processes (e.g., co-extrusion, over-extrusion, multilayer-extrusion) of the two elongate members 876, 888, and the circumferential orientation of each of the electrically-conductive tracings 884 is controlled with respect to the circumferential orientation of the conductors 880, 892.

In both the medical device body 850 of FIG. 28 and the medical device body 874 of FIG. 29, the circumferential space CS, CSD may include a sector of the medical device body 850, 874 that is between about 5° and about 180°, or between about 15° and about 120°, or between about 30° and about 90° or the total circumference or perimeter of the medical device body 850, 874. The word "perimeter" is intended to include cross-sections that are substantially non-circular. In some embodiments, the medical device bodies 850, 874 may also include additional lumens. In some embodiments, the medical device bodies 850, 874 may include additional shafts or tubes within their interior or around their exterior. These additional shafts or tubes may each include their own one or more electrically-conductive tracings or embedded conductors. The embedded conductors in come embodiments in the medical device bodies 850, 874 may extend through lumens. The electrically-conductive tracings and/or the conductors may extend substantially longitudinally, or may have a non-linear path, such as a serpentine path or a helical path.

The circumferential space CS, CSD is created by alignment of two or more nonuniform, unevenly dispersed arrays, comprising two or more or three or more electrically-conductive tracings and/or conductors. The orifices 870, 896 allow the passage of fluid from an internal lumen 856, 890 to an exterior of the medical device body 850, 874, for example, into tissue or a body lumen or cavity of a patient.

The medical device bodies 850, 874 or variations thereof may also be incorporated into any of the medical system embodiments described in FIGS. 19-27. The medical device bodies 800, 1000, 850, 874 described herein may be incorporated into a variety of medical devices, and may have a diameter or (if nor circular) a maximum transverse dimension of between about 0.5 mm and about 40 mm, or between about 1 mm and about 30 mm, or between about 2 mm and about 15 mm. As described, the medical devices incorporating these medical device bodies 800, 1000, 850, 874 may be configured for performing therapeutic procedures or diagnostic procedures, or for performing both, either at separate periods or at the same time. Though electrically-conductive tracings and elongate conductors are described herein, a similar configuration of conductive tracings and/or elongate wires may be used for more resistive tracings or wires. For example, resistive tracings on an external surface of a medical device body may be used to apply heat, for ablation, or to warm tissue or body or injected fluids, or to increase the activity of a drug. Resistive tracings may also be used to produce light for visualization or measurement. Resistive tracings may be used to measure temperature, for example to control a device from reaching high temperatures that might otherwise damage tissue, such as tissue of the esophagus. Resistive tracings may even be used to pace a heart.

Other medical applications, treatments, procedures, or devices therefor that may benefit from the medical device bodies 800, 1000, 850, 874 described herein include, but are not limited to the following: pacing leads; catheters or probes for imaging, including ultrasound, phased-array ultrasound, rotational ultrasound, forward looking ultrasound optical coherence tomography (OCT), infrared, near-infrared, electrophysiology mapping, thermographic imaging, elastographic imaging, catheters or probes for heating or energy delivery, including cancer treatment, sterilization of fallopian tube or other ducts, nerve ablation or therapy, cystic duct ablation, biliary duct ablation, lymph node ablation, urethral cancer treatment, neurovascular energy delivery for closure of aneurysms or arteriovenous malformations (AVMs), closure of heart defects such as patent foramen ovale (PFO), left atrial appendage (LAA), atrial septal defect (ASD), esophageal heating or energy application or ablation including Barrett's esophagus, gastroesophageal reflux disease (GERD), stimulation of reproductive system elements to increase fertility; laser imaging or treatment catheters or probes; heating of shape memory alloy elements in catheters or probes to cause shape change or movement therein; heating of internal elements in catheters or probes to cause shape memory polymers to heat and to change shape or cause motion.

While embodiments have been shown and described, various modifications may be made without departing from the scope of the inventive concepts disclosed herein.

"Externally-facing" is defined as facing toward an outward direction, but is not limited to a most external face. For example, an externally-facing surface may have one or more additional layers of tubing covering it. "Internally-facing" is defined as facing toward an inward direction, but is not limited to a most internal face. For example, an internally-facing surface may have one or more additional layers of tubing inside it.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A medical device for performing a diagnostic or therapeutic procedure within a subject, comprising:
    an elongate body comprising an outer elongate member comprising a polymeric material and having an outer surface, a proximal end, a distal end, and a lumen surrounded by a circumferential wall, the elongate body further comprising an inner elongate member extending within the lumen of the outer elongate member and having a proximal end, a distal end, and lumen surrounded by a circumferential wall, wherein the elongate body comprises a distal end configured to be inserted into a lumen or duct of the subject;
    first and second electrically-conductive tracings carried on the outer surface of the outer elongate member, the first electrically-conductive tracing electrically isolated from the second electrically-conductive tracing;
    first, second, and third elongate lumens extending longitudinally within the circumferential wall of the outer elongate member, the first, second, and third elongate lumens generally form a circumferential array;
    a first conductive wire extending substantially longitudinally within the first elongate lumen and configured to carry a first signal;
    a second conductive wire extending substantially longitudinally within the second elongate lumen and configured to carry a second signal;
    a third conductive wire extending substantially longitudinally within the third elongate lumen and configured to carry a third signal;
    wherein the first, second, and third conductive wires are located in a first sector of the circumferential wall of the outer elongate member, and wherein a second sector of the circumferential wall of the outer elongate member does not have any elongate conductive wires, such that the circumferential array of the first, second, and third elongate conductive wires is unevenly distributed around outer elongate member.

2. The medical device of claim 1, wherein the uneven distribution causes a circumferential space at the second sector that is about 5° to about 180° of the elongate body.

3. The medical device of claim 1, wherein the uneven distribution causes a circumferential space at the second sector that is about 15° to about 120° of the elongate body.

4. The medical device of claim 1, wherein the uneven distribution causes a circumferential space at the second sector that is about 30° to about 90° of the elongate body.

5. The medical device of claim 1, wherein at least a one of the first and second electrically-conductive tracings comprises an electrode.

6. The medical device of claim 1, wherein at least one of the first and second electrically conductive tracings comprises an elongate tracing extending substantially longitudinally along the outer surface of the outer elongate member.

7. The medical device of claim 6, wherein at least one of the first and second electrically-conductive tracings comprises an electrode.

8. The medical device of claim 7, wherein the electrode is electrically coupled to the at least one of the first and second electrically-conductive tracings.

9. The medical device of claim 7, wherein the electrode is electrically coupled to at least one of the first, second, and third conductive wires.

10. The medical device of claim 1, further comprising an orifice passing through the circumferential wall of the outer elongate member at the second sector.

11. The medical device of claim 10, wherein the orifice passes through the circumferential wall of the inner elongate member at the second sector.

12. The medical device of claim 1, wherein the first, second, and third elongate lumens are located in the first sector of the circumferential wall of the outer elongate member, and wherein the second sector of the circumferential wall of the outer elongate member does not have any elongate lumens.

13. The medical device of claim 12, wherein the second sector of the circumferential wall of the outer elongate member does not have any conductive wires.

14. The medical device of claim 1, wherein the first electrically conductive tracing comprises a first electrode and the second electrically conductive tracing comprises a second electrode, and wherein first and second electrodes are configured to measure a bio-impedance within the lumen or duct of the subject.

15. The medical device of claim 1, wherein the first and second electrically-conductive tracings each comprise an ink selected from the list consisting of: silver ink, carbon ink, silver-silver chloride ink, and silver-carbon silver chloride ink.

16. The medical device of claim 1, wherein the first and second electrically-conductive tracings each comprise radiopaque ink.

17. The medical device of claim 1, wherein the first, second, and third conductive wires each have a diameter of between about 0.004 inch and about 0.012 inch.

18. The medical device of claim 1, wherein each one of the first and second electrically conductive tracings comprises an elongate tracing extending substantially longitudinally along the outer surface of the outer elongate member from the proximal end of the outer elongate member to the distal end of the outer elongate member.

19. The medical device of claim 1, further comprising:
an elongate lumen extending longitudinally within the circumferential wall of the inner elongate member; and
a conductive wire extending substantially longitudinally within the elongate lumen of the inner elongate member and configured to carry a first signal.

20. The medical device of claim 1, wherein the elongate body has a circular outer cross-section.

* * * * *

UNITED STATES PATENT AND TRADEMARK OFFICE
CERTIFICATE OF CORRECTION

PATENT NO. : 11,375,953 B2
APPLICATION NO. : 17/013581
DATED : July 5, 2022
INVENTOR(S) : Guy Russell Lowery It is certified that error appears in the above-identified patent and that said Letters Patent is hereby corrected as shown below:

In the Claims

Column 26, Claim 1, Line 56: replace "form" with -- forming --

Signed and Sealed this
Twentieth Day of December, 2022

*Katherine Kelly Vidal*

Katherine Kelly Vidal
*Director of the United States Patent and Trademark Office*